US010259836B2

(12) United States Patent
Lim et al.

(10) Patent No.: US 10,259,836 B2
(45) Date of Patent: Apr. 16, 2019

(54) METHODS OF FORMING THIN FILM AND FABRICATING INTEGRATED CIRCUIT DEVICE USING NIOBIUM COMPOUND

(71) Applicants: SAMSUNG ELECTRONICS CO., LTD., Suwon-si, Gyeonggi-do (KR); L'Air Liquide, Societe Anonyme Pour L'etude et L'exploitation des Procedes Georges Claude, Paris (FR)

(72) Inventors: Jae-soon Lim, Seoul (KR); Gyu-hee Park, Hwaseong-si (KR); Youn-joung Cho, Hwaseong-si (KR); Clement Lansalot, Seoul (KR); Won-tae Noh, Seoul (KR); Julien Lieffrig, Seoul (KR); Joo-ho Lee, Seoul (KR)

(73) Assignees: Samsung Electronics Co., Ltd., Suwon-Si, Gyeonggi-do (KR); L'Air Liquide, Societe Anonyme Pour L'Etude Et L'Exploitation Des Procedes Georges Claude, Paris (FR)

(*) Notice: Subject to any disclaimer, the term of this patent is extended or adjusted under 35 U.S.C. 154(b) by 176 days.

(21) Appl. No.: 15/363,088

(22) Filed: Nov. 29, 2016

(65) Prior Publication Data
US 2017/0152277 A1 Jun. 1, 2017

(30) Foreign Application Priority Data

Nov. 30, 2015 (KR) .................. 10-2015-0169058

(51) Int. Cl.
| | | |
|---|---|---|
| C23C 16/28 | (2006.01) | |
| C07F 17/00 | (2006.01) | |
| C09D 5/24 | (2006.01) | |
| H01L 21/02 | (2006.01) | |
| H01L 21/28 | (2006.01) | |
| H01L 21/285 | (2006.01) | |
| H01L 27/108 | (2006.01) | |
| H01L 49/02 | (2006.01) | |
| H01L 29/49 | (2006.01) | |
| H01L 29/51 | (2006.01) | |
| H01L 29/66 | (2006.01) | |

(52) U.S. Cl.
CPC .............. *C07F 17/00* (2013.01); *C09D 5/24* (2013.01); *H01L 21/02189* (2013.01); *H01L 21/28088* (2013.01); *H01L 21/28556* (2013.01); *H01L 21/28568* (2013.01); *H01L 27/1085* (2013.01); *H01L 27/10855* (2013.01); *H01L 27/10879* (2013.01); *H01L 28/60* (2013.01); *H01L 29/4966* (2013.01); *H01L 29/517* (2013.01); *H01L 29/66795* (2013.01)

(58) Field of Classification Search
CPC .............. C23C 16/34; C23C 16/45536; C23C 16/45553; C23C 16/30; C01B 21/0617
See application file for complete search history.

(56) References Cited

U.S. PATENT DOCUMENTS

| 7,547,796 B2 | 6/2009 | Peters et al. |
| 7,572,731 B2 | 8/2009 | Millward et al. |
| 7,638,645 B2* | 12/2009 | Gordon ................. C07C 257/14 427/248.1 |
| 7,687,848 B2 | 3/2010 | Forbes et al. |
| 7,736,697 B2 | 6/2010 | Thompson et al. |
| 7,867,880 B2 | 1/2011 | Park et al. |
| 8,153,831 B2 | 4/2012 | Thompson et al. |
| 8,460,989 B2 | 6/2013 | Blasco et al. |
| 8,642,797 B2 | 2/2014 | Ivanov et al. |
| 8,809,849 B2 | 8/2014 | Pallem et al. |
| 10,023,462 B2* | 7/2018 | Lansalot-Matras ......................... C01B 21/0617 |
| 2007/0184366 A1* | 8/2007 | Takakuwa ............. G03F 7/0007 430/7 |
| 2008/0102205 A1* | 5/2008 | Barry ....................... C23C 16/18 427/250 |
| 2008/0254218 A1 | 10/2008 | Lei et al. |
| 2008/0272421 A1 | 11/2008 | Bhat |
| 2008/0305260 A1* | 12/2008 | Shenai-Khatkhate ...................... C23C 16/405 427/255.394 |
| 2013/0295778 A1 | 11/2013 | Blasco et al. |
| 2014/0106071 A1 | 4/2014 | Lansalot-Matras et al. |
| 2014/0175362 A1* | 6/2014 | Tendulkar ........... H01L 45/1253 257/4 |

FOREIGN PATENT DOCUMENTS

| EP | 1563117 B1 * | 1/2010 |
| EP | 2 174 942 B1 | 11/2011 |
| EP | 2810949 A1 * | 12/2014 |
| KR | 10-0936490 B1 | 1/2010 |

OTHER PUBLICATIONS

Miller, Gordon J., et al., "Chemistry and properties of novel niobium cluster compounds". Journal of Alloys and Compounds 229 (1995) 93-106.*
Boni, Gilles, et al., "Reactivity of bis(cyclopentadienyl)niobium and bis(cyclopentadienyl)tantalum trihydride . . . " Journal of Organometallic Chemistry 487 (1995) 105-109.*
Pizzol, P. et al., "Atomic Layer Deposition of Niobium Nitride from Different Precursors". Proceedings of IPAC2017, Copenhagen, Denmark, MOPVA100, 07 Accelrator Technology, T07 Superconducting RF, 2017, 1094-1097.*
Zauner, Andy, et al., "Niobium Precursors for Atomic Layer Deposition of Nb2O5". 217th ECS Meeting, Abstract #948, one page, no date available. Abstract Only.*

(Continued)

*Primary Examiner* — Bret P Chen
(74) *Attorney, Agent, or Firm* — Lee & Morse, P.C.

(57) ABSTRACT

A method of forming a thin film includes forming a niobium-containing film on a substrate by using a niobium precursor composition and a reactant, the niobium precursor composition including a niobium compound represented by Formula (1):

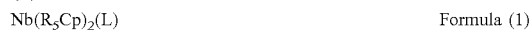

Formula (1)

(where each R is independently H, a C1 to C6 alkyl group, or $R^1_3Si$, with each $R^1$ being independently H or a C1 to C6 alkyl group, Cp is a cyclopentadienyl group, and L is a formamidinate, an amidinate, or a guanidinate.

20 Claims, 36 Drawing Sheets

(56) References Cited

OTHER PUBLICATIONS

Tomson, NC, et al., "Synthesis and reactivity of cationic niobium and tantalum methyl complexes supported by imido and B-diketiminato ligands". Dalton Trans. Aug. 14, 2011; 40(30):7718-29. Abstract Only.*

Mendes, F.M.T., et al., "Ammonium complex of niobium as a precursor for the preparation of NbO5/Al2O3 catalysts". Catalysis Today 78 (2003) 449-458.*

Chandler, Clive D., et al., "Chemical Aspects of Solution Routes to Perovskite-Phase Mixed-Metal Oxides from Metal-Organic Precursors". Chem. Rev. 1993, 93, 1205-1241.*

Hellwig, Malte, et al., "Stabilization of Amide-Based Complexes of Niobium and Tantalum Using Malonates as Chelating Ligands: Precursor Chemistry and Thin Film Deposition". Chem. Mater. 2007, 19, 6077-6087.*

Fitzsimmons, et al. "The Mossbauer Effect and Chemistry. Part 9. Molecular Motion in Solids. The Spectra of ($\eta$-Cyclohexatriene)($\eta$-cyclopentadienyl)iron(II) Hexafluorophosphate" J.C.S. Dalton (1980) pp. 180-186.

Elers, et al. "NbCI$_5$ As a Precursor in Atomic Layer Epitaxy" Applied Surface Science 82/83 (1994) pp. 468-474.

Ritala, et al. "Effects of Intermediate Zinc Pulses on Properties of TiN and NbN Films Deposited by Atomic Layer Epitaxy" Applied Surface Science 120 (1997) pp. 199-212.

Coles, et al. "Synthesis and Structures of Mono- and Bis(amidinate) Complexes of Aluminum" Organometallics 16 (1997) pp. 5183-5194.

Alen, et al. "The Growth and Diffusion Barrier Properties of Atomic Layer Deposited NbN$_x$ Thin Films" Thin Solid Films 491 (2005) pp. 235-241.

Cameron, et al. "Synthesis and Structure of Strontium and Barium Guanidinates and Mixed-Ligand Guanidinate Pentamethylcyclopentadienyl Complexes" Organometallics 27 (2008) pp. 1596-1604.

* cited by examiner

METHODS OF FORMING THIN FILM AND FABRICATING INTEGRATED CIRCUIT DEVICE USING NIOBIUM COMPOUND

CROSS-REFERENCE TO RELATED APPLICATION

Korean Patent Application No. 10-2015-0169058, filed on Nov. 30, 2015, in the Korean Intellectual Property Office, and entitled: "Methods of Forming Thin Film and Fabricating Integrated Circuit Device Using Niobium Compound," is incorporated by reference herein in its entirety.

BACKGROUND

1. Field

Embodiments relate to methods of forming a thin film and fabricating an integrated circuit device using a niobium compound.

2. Description of the Related Art

Due to the development of electronic technologies, downscaling of semiconductor devices is being quickly carried out in recent years, and thus, patterns constituting electronic devices are becoming finer.

SUMMARY

Embodiments are directed to a method of forming a thin film, the method including forming a niobium-containing film on a substrate by using a niobium precursor composition and a reactant, the niobium precursor composition including a niobium compound represented by Formula (1):

$$Nb(R_5Cp)_2(L) \qquad \text{Formula (1)}$$

wherein, in Formula (1), each R is independently H, a C1 to C6 alkyl group, or $R^1_3Si$, with each $R^1$ being independently H or a C1 to C6 alkyl group, Cp is a cyclopentadienyl group, and L is a formamidinate, an amidinate, or a guanidinate.

Embodiments are also directed to a method of fabricating an integrated circuit device, the method including forming a lower structure on a substrate, and forming a niobium-containing film on the lower structure by using a niobium precursor composition and a reactant, the niobium precursor composition including a niobium compound represented by Formula (1):

$$Nb(R_5Cp)_2(L) \qquad \text{Formula (1)}$$

wherein, in Formula (1), each R is independently H, a C1 to C6 alkyl group, or $R^1_3Si$, with each $R^1$ being independently H or a C1 to C6 alkyl group, Cp is a cyclopentadienyl group, and L is a formamidinate, an amidinate, or a guanidinate.

Embodiments are also directed to a method of forming a semiconductor device, the method including vaporizing a niobium compound represented by Formula (1) and supplying the vaporized niobium compound to a substrate, and reacting the niobium compound with a nitrogen-containing reactant to form an electrically conductive niobium nitride layer on the substrate, $$Nb(R_5Cp)_2(L) \qquad \text{Formula (1)}$$

wherein, in Formula (1), each R is independently H, a C1 to C6 alkyl group, or $R^1_3Si$, with each $R^1$ being independently H or a C1 to C6 alkyl group, Cp is a cyclopentadienyl group, and L is a formamidinate, an amidinate, or a guanidinate.

BRIEF DESCRIPTION OF THE DRAWINGS

Features will become apparent to those of skill in the art by describing in detail exemplary embodiments with reference to the attached drawings in which:

FIG. 24A is a plan view of an integrated circuit device that is intended to be formed, FIG. 24B is a perspective view of the integrated circuit device of FIG. 24A, and FIG. 24C respectively shows sectional views of the integrated circuit device taken along lines X-X' and Y-Y' of FIG. 24A.

DETAILED DESCRIPTION

Figure 1:
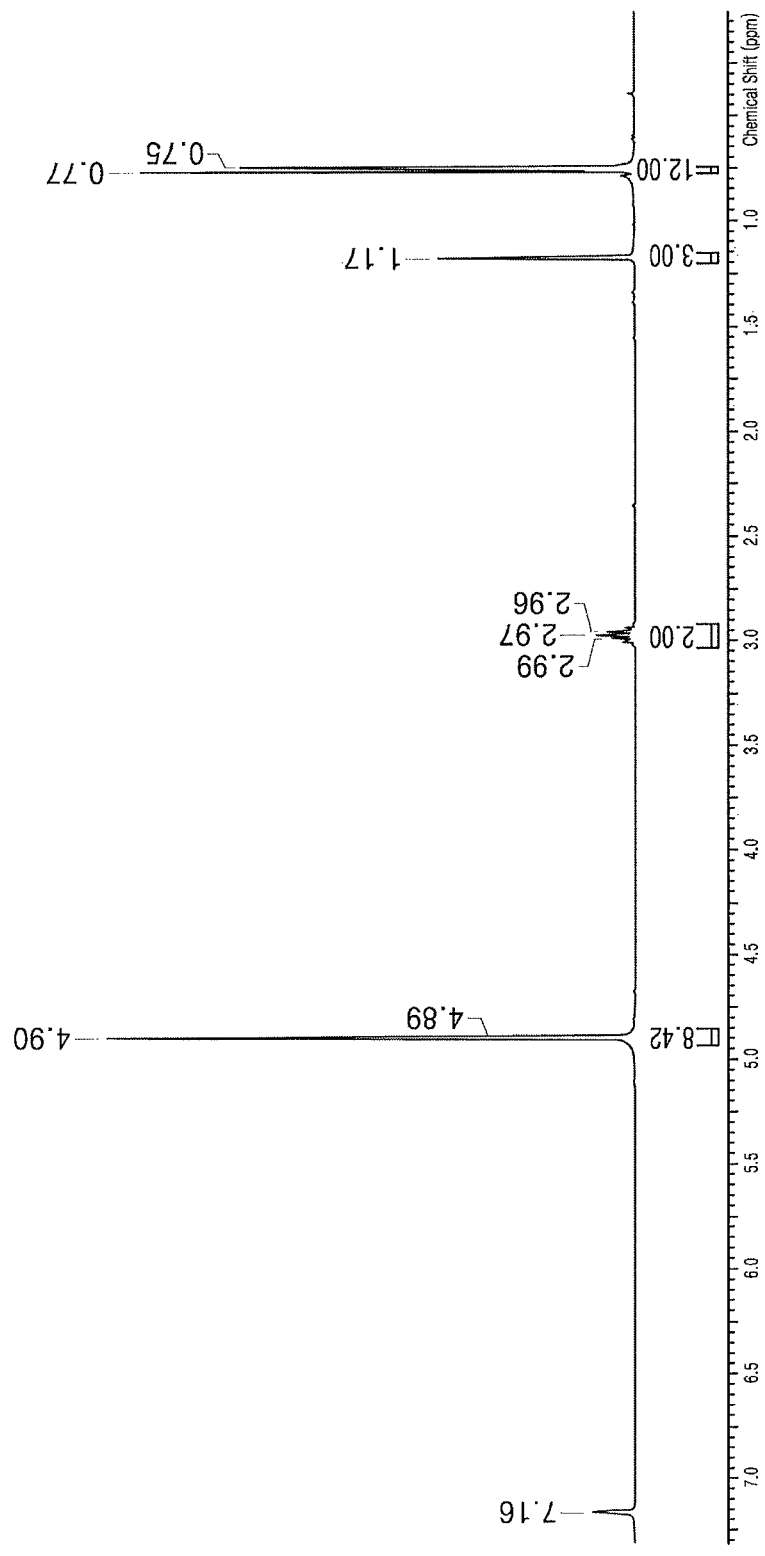
FIG. 1 illustrates a $^1$H-NMR (proton nuclear magnetic resonance) spectrum of bis-cyclopentadienyl diisopropylacetamidinato niobium ($NbCp_2(N^{iPr}$ Me-amd))

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. In the drawing figures, the dimensions of layers and regions may be exaggerated for clarity of illustration. Like reference numerals refer to like elements throughout.

As used herein, the term "approximately" or "about" means a range of ±10% of the stated value. The standard abbreviations of the elements from the periodic table of elements may be used herein. For example, Nb refers to niobium, N refers to nitrogen, and C refers to carbon. As used herein, the term "independently", when used in the context of describing R groups, should be understood to denote that the subject R group is not only independently selected relative to other R groups bearing the same or different subscripts or superscripts, but is also independently selected relative to any additional species of that same R group. For example, in the formula MR$^1_x$ (NR$^2$R$^3$)$_{(4-x)}$, where x is 2 or 3, the two or three R$^1$ groups may or may not be identical to each other.

As used herein, the term "alkyl group" refers to saturated functional groups containing exclusively carbon and hydrogen atoms. In addition, the term "alkyl group" refers to linear, branched, or cyclic alkyl groups. Examples of linear alkyl groups may include a methyl group, an ethyl group, a propyl group, a butyl group, and the like, without being limited thereto. Examples of branched alkyl groups may include a t-butyl group, without being limited thereto. Examples of cyclic alkyl groups may include a cyclopropyl group, a cyclopentyl group, a cyclohexyl group, and the like, without being limited thereto.

As used herein, the abbreviation "Me" refers to a methyl group; the abbreviation "Et" refers to an ethyl group; the abbreviation "Pr" refers to a propyl group; the abbreviation "nPr" refers to a normal or linear propyl group; the abbreviation "iPr" refers to an isopropyl group; the abbreviation "Bu" refers to a butyl group; the abbreviation "nBu" refers to a normal or linear butyl group; the abbreviation "tBu" refers to a tert-butyl group (1,1-dimethylethyl group); the abbreviation "sBu" refers to a sec-butyl group (1-methylpropyl group); the abbreviation "iBu" refers to an iso-butyl group (2-methylpropyl group); the term "amyl" refers to an amyl or pentyl group; and the abbreviation "tAmyl" or "tAm" refers to a tert-amyl group (1,1-dimethylpropyl group).

As used herein, the abbreviation "Cp" refers to a cyclopentadienyl group; the abbreviation "Cp*" refers to a pentamethylcyclopentadienyl group; and the abbreviation "TMS" refers to trimethylsilyl (Me$_3$Si—).

As used herein, the abbreviation "N$^{R,\ R'}$-fmd" or "N$^R$-fmd" (when R=R') refers to a formamidinate ligand [R—N—C(H)=N—R'] as represented by Chemical Formula 4, wherein R and R' are alkyl groups, for example, Me, Et, nPr, iPr, nBu, iBu, sBu, or tBu.

[Chemical Formula 4]

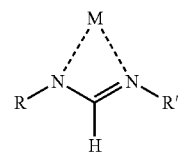

As used herein, the abbreviation "N$^{R,\ R'}$R"-amd" or "N$^R$R"-amd" (when R=R') refers to an amidinate ligand [R—N—C(R")=N—R'] as represented by Chemical Formula 5, wherein R, R', and R" are alkyl groups, for example, Me, Et, nPr, iPr, nBu, iBu, sBu, or tBu.

[Chemical Formula 5]

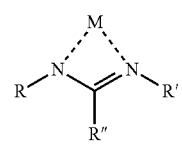

As used herein, the abbreviation "N$^{R,\ R'}$, N$^{R",\ R'''}$-gnd" or "N$^R$, N$^{R"}$-gnd" (when R=R' and R"=R''') refers to a guanidinate ligand [R—N—C(NR"R''')=NR'] as represented by Chemical Formula 6, wherein R, R', R", and R''' are alkyl groups, for example, Me, Et, nPr, iPr, nBu, iBu, sBu, or tBu.

[Chemical Formula 6]

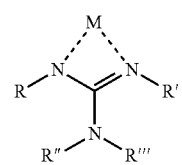

In Chemical Formulae 4, 5, and 6, M is a central metal, for example, Nb.

Herein, although the ligands described above are shown as having a double bond between C and N of a ligand backbone, those of skill in the art will recognize that each of the formamidinate, amidinate, and guanidinate ligands does not include a fixed double bond, and that one electron is delocalized among the N—C—N chain.

According to an example embodiment, a niobium compound may be represented by Formula (1):

Nb(R$_5$Cp)$_2$(L)     Formula (1)

wherein, in R₅Cp

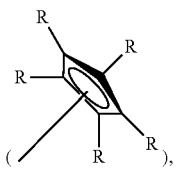

each R is independently H, a C1 to C6 alkyl group, or R¹₃Si, with each R¹ being independently H or a C1 to C6 alkyl group; and Cp is a cyclopentadienyl group. The alkyl group may be a methyl, ethyl, propyl, butyl, or pentyl group. L is selected from among formamidinates (N$^{R,\ R'}$-fmd), amidinates (N$^{R,\ R'}$ R''-amd), and guanidinates (N$^{R,\ R'}$, N$^{R'',\ R'''}$-gnd).

In some embodiments, L is a formamidinate, and the niobium compound according to Formula (1) may be represented by Chemical Formula 1:

[Chemical Formula 1]

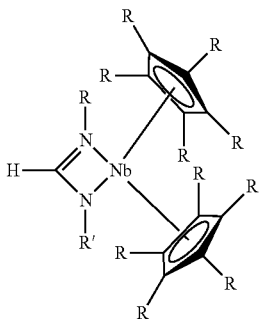

wherein R and R' are each independently H, a C1 to C6 alkyl group, or R¹₃Si, with each R¹ being defined as above.

The niobium compound according to Chemical Formula 1 may be represented by Formula (2):

Nb(R₅Cp)₂(N$^{R,R'}$-fmd)   Formula (2)

wherein R and R' are each independently H, a C1 to C6 alkyl group, or R¹₃Si, with each R¹ being independently H or a C1 to C6 alkyl group. When R=R', Formula (2) may be expressed as Nb(R₅Cp)₂(N$^{R}$-fmd).

In some embodiments, the niobium compound according to Chemical Formula 1 may be Nb(Cp)₂(N$^{Me}$-fmd), Nb(Cp)₂ (N$^{Et}$-fmd), Nb(Cp)₂(N$^{iPr}$-fmd), Nb(Cp)₂(N$^{nPr}$-fmd), Nb(Cp)₂(N$^{iBu}$-fmd), Nb(Cp)₂(N$^{nBu}$-fmd), Nb(Cp)₂ (N$^{tBu}$-fmd), Nb(Cp)₂(N$^{sBu}$-fmd), Nb(Cp)₂(N$^{tAm}$-fmd), Nb(Cp)₂(N$^{TMS}$-fmd), Nb(MeCp)₂(N$^{Me}$-fmd), Nb(MeCp)₂ (N$^{Et}$-fmd), Nb(MeCp)₂(N$^{iPr}$-fmd), Nb(MeCp)₂(N$^{nPr}$-fmd), Nb(MeCp)₂(N$^{iBu}$-fmd), Nb(MeCp)₂(N$^{nBu}$-fmd), Nb (MeCp)₂ (N$^{tBu}$-fmd), Nb(MeCp)₂(N$^{sBu}$-fmd), Nb(MeCp)₂ (N$^{tAm}$-fmd), Nb(MeCp)₂(N$^{TMS}$-fmd), Nb(EtCp)₂ (N$^{Me}$-fmd), Nb(EtCp)₂(N$^{Et}$-fmd), Nb(EtCp)₂(N$^{iPr}$-fmd), Nb(EtCp)₂(N$^{nPr}$-fmd), Nb(EtCp)₂(N$^{iBu}$-fmd), Nb(EtCp)₂ (N$^{nBu}$-fmd), Nb(EtCp)₂(N$^{tBu}$-fmd), Nb(EtCp)₂(N$^{sBu}$-fmd), Nb(EtCp)₂(N$^{tAm}$-fmd), Nb(EtCp)₂(N$^{TMS}$-fmd), Nb(iPrCp)₂ (N$^{Me}$-fmd), Nb(iPrCp)₂(N$^{Et}$-fmd), Nb(iPrCp)₂(N$^{iPr}$-fmd), Nb(iPrCp)₂(N$^{nPr}$-fmd), Nb(iPrCp)₂(N$^{iBu}$-fmd), Nb(iPrCp)₂ (N$^{nBu}$-fmd), Nb(iPrCp)₂(N$^{tBu}$-fmd), Nb(iPrCp)₂(N$^{sBu}$-fmd), Nb(iPrCp)₂(N$^{tAm}$-fmd), Nb(iPrCp)₂(N$^{TMS}$-fmd), Nb(tBuCp)₂ (N$^{Me}$-fmd), Nb(tBuCp)₂(N$^{Et}$-fmd), Nb (tBuCp)₂ (N$^{iPr}$-fmd), Nb(tBuCp)₂(N$^{nPr}$-fmd), Nb(tBuCp)₂ (N$^{iBu}$-fmd), Nb(tBuCp)₂(N$^{nBu}$-fmd), Nb(tBuCp)₂(N$^{tBu}$-fmd), Nb(tBuCp)₂(N$^{sBu}$-fmd), Nb(tBuCp)₂(N$^{tAm}$-fmd), Nb(tBuCp)₂(N$^{TMS}$-fmd), Nb(iPr₃Cp)₂(N$^{Me}$-fmd), Nb (iPr₃Cp)₂(N$^{Et}$-fmd), Nb(iPr₃Cp)₂(N$^{iPr}$-fmd), Nb(iPr₃Cp)₂ (N$^{nPr}$-fmd), Nb(iPr₃Cp)₂(N$^{iBu}$-fmd), Nb(iPr₃Cp)₂(N$^{nBu}$-fmd), Nb(iPr₃Cp)₂(N$^{tBu}$-fmd), Nb(iPr₃Cp)₂(N$^{sBu}$-fmd), Nb(iPr₃Cp)₂(N$^{tAm}$-fmd), Nb(iPr₃Cp)₂(N$^{TMS}$-fmd), Nb(Cp*)₂ (N$^{Me}$-fmd), Nb(Cp*)₂(N$^{Et}$-fmd), Nb(Cp*)₂(N$^{iPr}$-fmd), Nb(Cp*)₂(N$^{nPr}$-fmd), Nb(Cp*)₂(N$^{iBu}$-fmd), Nb(Cp*)₂ ($^{nBu}$-fmd), Nb(Cp*)₂($^{tBu}$-fmd), Nb(Cp*)₂(N$^{sBu}$-fmd), Nb(Cp*)₂(N$^{tAm}$-fmd), Nb(Cp*)₂(N$^{TMS}$-fmd), Nb (Me₃SiCp)₂(N$^{Me}$-fmd), Nb(Me₃SiCp)₂(N$^{Et}$-fmd), Nb(Me₃SiCp)₂(N$^{iPr}$-fmd), Nb(Me₃SiCp)₂(N$^{nPr}$-fmd), Nb(Me₃SiCp)₂(N$^{iBu}$-fmd), Nb(Me₃SiCp)₂(N$^{nBu}$-fmd), Nb(Me₃SiCp)₂(N$^{tBu}$-fmd), Nb(Me₃SiCp)₂(N$^{sBu}$-fmd), Nb(Me₃SiCp)₂(N$^{tAm}$-fmd), Nb(Me₃SiCp)₂(N$^{TMS}$-fmd), Nb(Cp)(Cp*)(N$^{Me}$-fmd), Nb(Cp)(iPr₃Cp)(N$^{Me}$-fmd), Nb(Cp)(MeCp) (N$^{Et}$-fmd), Nb(Cp)(EtCp)(N$^{iPr}$-fmd), Nb(Cp)(iPrCp)(N$^{nPr}$-fmd), Nb(Cp)(nPrCp)(N$^{iBu}$-fmd), Nb(Cp)(iBuCp)(N$^{nBu}$-fmd), Nb(Cp)(tBuCp)(N$^{tBu}$-fmd), Nb(Cp)(tAmCp)(N$^{sBu}$-fmd), Nb(iPr₃Cp)(Cp)(N$^{Et}$-fmd), Nb(Cp)₂(N$^{Et,\ tBu}$-fmd), Nb(MeCp)₂(N$^{Et,\ tBu}$-fmd), Nb(EtCp)₂(N$^{Et,\ tBu}$-fmd), Nb(iPrCp)₂(N$^{Et,\ tBu}$-fmd), Nb(tBuCp)₂(N$^{Et,\ tBu}$-fmd), Nb(iPr₃Cp)₂ (N$^{Et,\ tBu}$-fmd), Nb(Cp*)(N$^{Et,\ tBu}$-fmd), or Nb(Me₃SiCp)₂ (N$^{Et,\ tBu}$-fmd).

The niobium compound according to Chemical Formula 1 may be synthesized by, for example, reacting Nb(R₅Cp)₂X₂ with 2 equivalents of Z(N$^{R,\ R'}$-fmd). Here, X may be selected from among halogen elements F, Cl, Br, and I; Z may be selected from among alkali metal elements Li, Na, and K; and R and R' may be each independently H, Me, Et, nPr, iPr, tBu, sBu, iBu, nBu, tAmyl, SiMe₃, SiMe₂H, or SiH₂Me. Nb(R₅Cp)₂X₂ may be synthesized as described in J. C. S. Dalton 1980, 180-186. Z(N$^{R,\ R'}$-fmd) may be synthesized by a reaction of an alkyl alkali metal, for example, n-butyl lithium (nBuLi) with a formamidine molecule. The formamidine molecule may be synthesized according to the procedure described in Organometallics 2004, 23, 3512-3520. A reactant may be added at a low temperature that is less than −50° C. The reaction may be performed in a polar solvent, for example, THF, or diethyl ether. The niobium compound may be separated from an alkali salt by extraction using a non-polar solvent, such as pentane, hexane, cyclohexane, heptane, benzene, toluene, and the like. A result product including the synthesized niobium compound may be purified by vacuum sublimation, by vacuum distillation, or by recrystallization in an appropriate solvent selected from among THF, diethyl ether, pentane, hexane, cyclohexane, heptane, benzene, toluene, and mixtures thereof.

In some embodiments, the niobium compound according to Chemical Formula 1 may be a liquid at room temperature. As used herein, the term "room temperature" refers to a temperature ranging from about 20° C. to about 28° C., and may vary with the seasons.

In some embodiments, L is an amidinate, and the niobium compound according to Formula (1) may be represented by Chemical Formula 2:

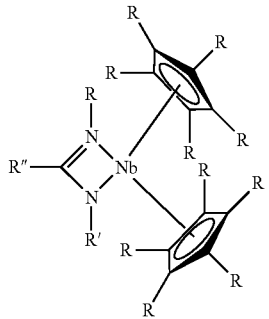

[Chemical Formula 2]

wherein R, R', and R" are each independently H, a C1 to C6 alkyl group, or $R^1{}_3Si$, with each $R^1$ being defined as above. The alkyl group may be a methyl, ethyl, propyl, butyl, or pentyl group.

The niobium compound according to Chemical Formula 2 may be represented by Formula (3):

$$Nb(R_5Cp)_2(N^{R,R'}R''\text{-amd}) \qquad \text{Formula (3)}$$

wherein R, R', and R" are each independently H, a C1 to C6 alkyl group, or $R^1{}_3Si$, with each $R^1$ being defined as above. When R=R', Formula (3) may be expressed as $Nb(R_5Cp)_2(N^R R''\text{-amd})$.

In some embodiments, the niobium compound according to Chemical Formula 2 may be $Nb(Cp)_2(N^{Me}$ Me-amd), $Nb(Cp)_2(N^{Et}$ Me-amd), $Nb(Cp)_2(N^{iPr}$ Me-amd), $Nb(Cp)_2(N^{nPr}$ Me-amd), $Nb(Cp)_2(N^{iBu}$ Me-amd), $Nb(Cp)_2(N^{nBu}$ Me-amd), $Nb(Cp)_2(N^{tBu}$ Me-amd), $Nb(Cp)_2(N^{sBu}$ Me-amd), $Nb(Cp)_2(N^{tAm}$ Me-amd), $Nb(Cp)_2(N^{TMS}$ Me-amd), $Nb(MeCp)_2(N^{Me}$ Me-amd), $Nb(MeCp)_2(N^{Et}$ Me-amd), $Nb(MeCp)_2(N^{iPr}$ Me-amd), $Nb(MeCp)_2(N^{nPr}$ Me-amd), $Nb(MeCp)_2(N^{iBu}$ Me-amd), $Nb(MeCp)_2(N^{nBu}$ Me-amd), $Nb(MeCp)_2(N^{tBu}$ Me-amd), $Nb(MeCp)_2(N^{sBu}$ Me-amd), $Nb(MeCp)_2(N^{tAm}$ Me-amd), $Nb(MeCp)_2(N^{TMS}$ Me-amd), $Nb(EtCp)_2(N^{Me}$ Me-amd), $Nb(EtCp)_2(N^{Et}$ Me-amd), $Nb(EtCp)_2(N^{iPr}$ Me-amd), $Nb(EtCp)_2(N^{nPr}$ Me-amd), $Nb(EtCp)_2(N^{iBu}$ Me-amd), $Nb(EtCp)_2(N^{nBu}$ Me-amd), $Nb(EtCp)_2(N^{tBu}$ Me-amd), $Nb(EtCp)_2(N^{sBu}$ Me-amd), $Nb(EtCp)_2(N^{tAm}$ Me-amd), $Nb(EtCp)_2(N^{TMS}$ Me-amd), $Nb(iPrCp)_2(N^{Me}$ Me-amd), $Nb(iPrCp)_2(N^{Et}$ Me-amd), $Nb(iPrCp)_2(N^{iPr}$ Me-amd), $Nb(iPrCp)_2(N^{nPr}$ Me-amd), $Nb(iPrCp)_2(N^{iBu}$ Me-amd), $Nb(iPrCp)_2(N^{nBu}$ Me-amd), $Nb(iPrCp)_2(N^{tBu}$ Me-amd), $Nb(iPrCp)_2(N^{sBu}$ Me-amd), $Nb(iPrCp)_2(N^{tAm}$ Me-amd), $Nb(iPrCp)_2(N^{TMS}$ Me-amd), $Nb(tBuCp)_2(N^{Me}$ Me-amd), $Nb(tBuCp)_2(N^{Et}$ Me-amd), $Nb(tBuCp)_2(N^{iPr}$ Me-amd), $Nb(tBuCp)_2(N^{nPr}$ Me-amd), $Nb(tBuCp)_2(N^{iBu}$ Me-amd), $Nb(tBuCp)_2(N^{nBu}$ Me-amd), $Nb(tBuCp)_2(N^{tBu}$ Me-amd), $Nb(tBuCp)_2(N^{sBu}$ Me-amd), $Nb(tBuCp)_2(N^{tAm}$ Me-amd), $Nb(tBuCp)_2(N^{TMS}$ Me-amd), $Nb(iPr_3Cp)_2(N^{Me}$ Me-amd), $Nb(iPr_3Cp)_2(N^{Et}$ Me-amd), $Nb(iPr_3Cp)_2(N^{iPr}$ Me-amd), $Nb(iPr_3Cp)_2(N^{nPr}$ Me-amd), $Nb(iPr_3Cp)_2(N^{iBu}$ Me-amd), $Nb(iPr_3Cp)_2(N^{nBu}$ Me-amd), $Nb(iPr_3Cp)_2(N^{tBu}$ Me-amd), $Nb(iPr_3Cp)_2(N^{sBu}$ Me-amd), $Nb(iPr_3Cp)_2(N^{tAm}$ Me-amd), $Nb(iPr_3Cp)_2(N^{TMS}$ Me-amd), $Nb(Cp^*)_2(N^{Me}$ Me-amd), $Nb(Cp^*)_2(N^{Et}$ Me-amd), $Nb(Cp^*)_2(N^{iPr}$ Me-amd), $Nb(Cp^*)_2(N^{nPr}$ Me-amd), $Nb(Cp^*)_2(N^{iBu}$ Me-amd), $Nb(Cp^*)_2(N^{nBu}$ Me-amd), $Nb(Cp^*)_2(N^{tBu}$ Me-amd), $Nb(Cp^*)_2(N^{sBu}$ Me-amd), $Nb(Cp^*)_2(N^{tAm}$ Me-amd), $Nb(Cp^*)_2(N^{TMS}$ Me-amd), $Nb(Me_3SiCp)_2(N^{Me}$ Me-amd), $Nb(Me_3SiCp)_2(N^{Et}$ Me-amd), $Nb(Me_3SiCp)_2(N^{iPr}$ Me-amd), $Nb(Me_3SiCp)_2(N^{nPr}$ Me-amd), $Nb(Me_3SiCp)_2(N^{iBu}$ Me-amd), $Nb(Me_3SiCp)_2(N^{nBu}$ Me-amd), $Nb(Me_3SiCp)_2(N^{tBu}$ Me-amd), $Nb(Me_3SiCp)_2(N^{sBu}$ Me-amd), $Nb(Me_3SiCp)_2(N^{tAm}$ Me-amd), $Nb(Me_3SiCp)_2(N^{TMS}$ Me-amd), $Nb(Cp)(Cp^*)(N^{Me}$ Me-amd), $Nb(Cp)(iPr_3Cp)(N^{Me}$ Me-amd), $Nb(Cp)(MeCp)(N^{Et}$ Me-amd), $Nb(Cp)(EtCp)(N^{iPr}$ Me-amd), $Nb(Cp)(iPrCp)(N^{nPr}$ Me-amd), $Nb(Cp)(nPrCp)(N^{iBu}$ Me-amd), $Nb(Cp)(iBuCp)(N^{nBu}$ Me-amd), $Nb(Cp)(tBuCp)(N^{tBu}$ Me-amd), $Nb(Cp)(tAmCp)(N^{sBu}$ Me-amd), $Nb(Cp)_2(N^{iPr}$ Et-amd), $Nb(Cp)_2(N^{iPr}$ nPr-amd), $Nb(Cp)_2(N^{iPr}$ iPr-amd), $Nb(Cp)_2(N^{iPr}$ tBu-amd), $Nb(Cp)_2(N^{iPr}$ nBu-amd), $Nb(Cp)_2(N^{iPr}$ iBu-amd), $Nb(Cp)_2(N^{iPr}$ sBu-amd), $Nb(MeCp)_2(N^{iPr}$ Et-amd), $Nb(MeCp)_2(N^{iPr}$ nPr-amd), $Nb(MeCp)_2(N^{iPr}$ iPr-amd), $Nb(MeCp)_2(N^{iPr}$ tBu-amd), $Nb(MeCp)_2(N^{iPr}$ nBu-amd), $Nb(MeCp)_2(N^{iPr}$ iBu-amd), $Nb(MeCp)_2(N^{iPr}$ sBu-amd), $Nb(EtCp)_2(N^{iPr}$ Et-amd), $Nb(EtCp)_2(N^{iPr}$ nPr-amd), $Nb(EtCp)_2(N^{iPr}$ iPr-amd), $Nb(EtCp)_2(N^{iPr}$ tBu-amd), $Nb(EtCp)_2(N^{iPr}$ nBu-amd), $Nb(EtCp)_2(N^{iPr}$ iBu-amd), $Nb(EtCp)_2(N^{iPr}$ sBu-amd), $Nb(MeCp)_2(N^{Et, tBu}$ Me-amd), $Nb(EtCp)_2(N^{Et, tBu}$ Me-amd), $Nb(iPrCp)_2(N^{Et, tBu}$ Me-amd), $Nb(tBuCp)_2(N^{Et, tBu}$ Me-amd), $Nb(iPr_3Cp)_2(N^{Et, tBu}$ Me-amd), $Nb(Cp^*)_2(N^{Et, tBu}$ Me-amd), $Nb(Me_3SiCp)_2(N^{Et, tBu}$ Me-amd), $Nb(Cp)(iPr_3Cp)_2(N^{iPr}$ Me-amd), $Nb(Cp)_2(N^{iPr}$ sBu-amd), $Nb(iPr_3Cp)_2(N^{iPr}$ Et-amd), $Nb(iPr_3Cp)_2(N^{iPr}$ Me-amd), $Nb(iPr_3Cp)_2(N^{iPr}$ nPr-amd), $Nb(iPr_3Cp)_2(N^{iPr}$ iPr-amd), $Nb(iPr_3Cp)_2(N^{iPr}$ nBu-amd), $Nb(iPr_3Cp)_2(N^{iPr}$ tBu-amd), $Nb(iPr_3Cp)_2(N^{iPr}$ sBu-amd), or $Nb(iPr_3Cp)_2(N^{iPr}$ iBu-amd).

The niobium compound according to Chemical Formula 2 may be synthesized by reacting $Nb(R_5Cp)_2X_2$ with 2 equivalents of $Z(N^{R, R'}R''\text{-amd})$. Here, X may be selected from among halogen elements consisting of F, Cl, Br, and I; Z may be selected from among alkali metal elements consisting of Li, Na, and K; and R, R', and R" may be each independently H, Me, Et, nPr, iPr, tBu, sBu, iBu, nBu, tAmyl, $SiMe_3$, $SiMe_2H$, or $SiH_2Me$. $Nb(R_5Cp)_2X_2$ may be synthesized as described in J. C. S. Dalton 1980, 180-186. $Z(N^{R, R'}R''\text{-amd})$ may be prepared as described in Organometallics 1997, 16, 5183-5194. A reactant may be added at a low temperature of −50° C. The reaction may be performed in a polar solvent, for example, THF, or diethyl ether. The niobium compound may be separated from an alkali salt by extraction using a non-polar solvent, such as pentane, hexane, cyclohexane, heptane, benzene, toluene, and the like. A result product including the synthesized niobium compound may be purified by vacuum sublimation, by vacuum distillation, or by recrystallization in an appropriate solvent selected from among THF, diethyl ether, pentane, hexane, cyclohexane, heptane, benzene, toluene, and mixtures thereof.

In some embodiments, the niobium compound according to Chemical Formula 2 may be a liquid at room temperature.

In some embodiments, L is a guanidinate, and the niobium compound according to Formula (1) may be represented by Chemical Formula 3:

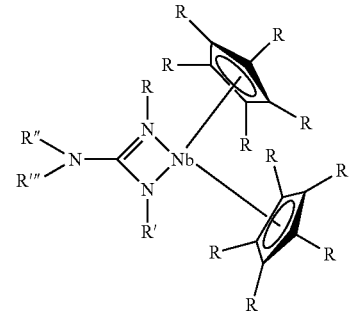

[Chemical Formula 3]

wherein R, R', R", and R''' are each independently H, a C1 to C6 alkyl group, or $R^1{}_3Si$, with each $R^1$ being defined as above. The alkyl group may be a methyl, ethyl, propyl, butyl, or pentyl group.

The niobium compound according to Chemical Formula 3 may be represented by Formula (4):

$Nb(R_5Cp)_2(N^{R,R'},N^{R'',R'''}\text{-gnd})$ wherein R, R', R", and R''' are each independently H, a C1 to C6 alkyl group, or $R^1{}_3Si$, with each $R^1$ being defined as above. When R=R' and R"=R''', Formula (4) may be expressed as $Nb(R_5Cp)_2(N^R, N^{R'''}\text{-gnd})$.

In some embodiments, the niobium compound according to Chemical Formula 3 may be $Nb(Cp)_2(N^{Me}, N^{Me}\text{-gnd})$, $Nb(Cp)_2(N^{Et}, N^{Me}\text{-gnd})$, $Nb(Cp)_2(N^{iPr}, N^{Me}\text{-gnd})$, $Nb(Cp)_2(N^{nPr}, N^{Me}\text{-gnd})$, $Nb(Cp)_2(N^{iBu}, N^{Me}\text{-gnd})$, $Nb(Cp)_2(N^{nBu}, N^{Me}\text{-gnd})$, $Nb(Cp)_2(N^{tBu}, N^{Me}\text{-gnd})$, $Nb(Cp)_2(N^{sBu}, N^{Me}\text{-gnd})$, $Nb(Cp)_2(N^{tAm}, N^{Me}\text{-gnd})$, $Nb(Cp)_2(N^{TMS}, N^{Me}\text{-gnd})$, $Nb(Cp)_2(N^{Et, tBu}, N^{Me}\text{-gnd})$, $Nb(MeCp)_2(N^{Me}, N^{Me}\text{-gnd})$, $Nb(MeCp)_2(N^{Et}, N^{Me}\text{-gnd})$, $Nb(MeCp)_2(N^{iPr}, N^{Me}\text{-gnd})$, $Nb(MeCp)_2(N^{nPr}, N^{Me}\text{-gnd})$, $Nb(MeCp)_2(N^{iBu}, N^{Me}\text{-gnd})$, $Nb(MeCp)_2(N^{nBu}, N^{Me}\text{-gnd})$, $Nb(MeCp)_2(N^{tBu}, N^{Me}\text{-gnd})$, $Nb(MeCp)_2(N^{sBu}, N^{Me}\text{-gnd})$, $Nb(MeCp)_2(N^{tAm}, N^{Me}\text{-gnd})$, $Nb(MeCp)_2(N^{TMS}, N^{Me}\text{-gnd})$, $Nb(MeCp)_2(N^{Et, tBu}, N^{Me}\text{-gnd})$, $Nb(EtCp)_2(N^{Me}, N^{Me}\text{-gnd})$, $Nb(EtCp)_2(N^{Et}, N^{Me}\text{-gnd})$, $Nb(EtCp)_2(N^{iPr}, N^{Me}\text{-gnd})$, $Nb(EtCp)_2(N^{nPr}, N^{Me}\text{-gnd})$, $Nb(EtCp)_2(N^{iBu}, N^{Me}\text{-gnd})$, $Nb(EtCp)_2(N^{nBu}, N^{Me}\text{-gnd})$, $Nb(EtCp)_2(N^{tBu}, N^{Me}\text{-gnd})$, $Nb(EtCp)_2(N^{sBu}, N^{Me}\text{-gnd})$, $Nb(EtCp)_2(N^{tAm}, N^{Me}\text{-gnd})$, $Nb(EtCp)_2(N^{TMS}, N^{Me}\text{-gnd})$, $Nb(EtCp)_2(N^{Et, tBu}, N^{Me}\text{-gnd})$, $Nb(iPrCp)_2(N^{Me}, N^{Me}\text{-gnd})$, $Nb(iPrCp)_2(N^{Et}, N^{Me}\text{-gnd})$, $Nb(iPrCp)_2(N^{iPr}, N^{Me}\text{-gnd})$, $Nb(iPrCp)_2(N^{nPr}, N^{Me}\text{-gnd})$, $Nb(iPrCp)_2(N^{iBu}, N^{Me}\text{-gnd})$, $Nb(iPrCp)_2(N^{nBu}, N^{Me}\text{-gnd})$, $Nb(iPrCp)_2(N^{tBu}, N^{Me}\text{-gnd})$, $Nb(iPrCp)_2(N^{sBu}, N^{Me}\text{-gnd})$, $Nb(iPrCp)_2(N^{tAm}, N^{Me}\text{-gnd})$, $Nb(iPrCp)_2(N^{TMS}, N^{Me}\text{-gnd})$, $Nb(iPrCp)_2(N^{Et, tBu}, N^{Me}\text{-gnd})$, $Nb(tBuCp)_2(N^{Me}, N^{Me}\text{-gnd})$, $Nb(tBuCp)_2(N^{Et}, N^{Me}\text{-gnd})$, $Nb(tBuCp)_2(N^{iPr}, N^{Me}\text{-gnd})$, $Nb(tBuCp)_2(N^{nPr}, N^{Me}\text{-gnd})$, $Nb(tBuCp)_2(N^{iBu}, N^{Me}\text{-gnd})$, $Nb(tBuCp)_2(N^{nBu}, N^{Me}\text{-gnd})$, $Nb(tBuCp)_2(N^{tBu}, N^{Me}\text{-gnd})$, $Nb(tBuCp)_2(N^{sBu}, N^{Me}\text{-gnd})$, $Nb(tBuCp)_2(N^{tAm}, N^{Me}\text{-gnd})$, $Nb(tBuCp)_2(N^{TMS}, N^{Me}\text{-gnd})$, $Nb(tBuCp)_2(N^{Et, tBu}, N^{Me}\text{-gnd})$, $Nb(iPrCp)_2(N^{Et}, N^{Me}\text{-gnd})$, $Nb(iPr_3Cp)_2(N^{Et}, N^{Me}\text{-gnd})$, $Nb(iPr_3Cp)_2(N^{iPr}, N^{Me}\text{-gnd})$, $Nb(iPr_3Cp)_2(N^{nPr}, N^{Me}\text{-gnd})$, $Nb(iPr_3Cp)_2(N^{iBu}, N^{Me}\text{-gnd})$, $Nb(iPr_3Cp)_2(N^{nBu}, N^{Me}\text{-gnd})$, $Nb(iPr_3Cp)_2(N^{tBu}, N^{Me}\text{-gnd})$, $Nb(iPr_3Cp)_2(N^{sBu}, N^{Me}\text{-gnd})$, $Nb(iPr_3Cp)_2(N^{tAm}, N^{Me}\text{-gnd})$, $Nb(iPr_3Cp)_2(N^{TMS}, N^{Me}\text{-gnd})$, $Nb(iPr_3Cp)_2(N^{Et, tBu}, N^{Me}\text{-gnd})$, $Nb(Cp^*)_2(N^{Me}, N^{Me}\text{-gnd})$, $Nb(Cp^*)_2(N^{Et}, N^{Me}\text{-gnd})$, $Nb(Cp^*)_2(N^{iPr}, N^{Me}\text{-gnd})$, $Nb(Cp^*)_2(N^{nPr}, N^{Me}\text{-gnd})$, $Nb(Cp^*)_2(N^{iBu}, N^{Me}\text{-gnd})$, $Nb(Cp^*)_2(N^{nBu}, N^{Me}\text{-gnd})$, $Nb(Cp^*)_2(N^{tBu}, N^{Me}\text{-gnd})$, $Nb(Cp^*)_2(N^{sBu}, N^{Me}\text{-gnd})$, $Nb(Cp^*)_2(N^{tAm}, N^{Me}\text{-gnd})$, $Nb(Cp^*)_2(N^{TMS}, N^{Me}\text{-gnd})$, $Nb(Cp^*)_2(N^{Et, tBu}, N^{Me}\text{-gnd})$, $Nb(Me_3SiCp)_2(N^{Me}, N^{Me}\text{-gnd})$, $Nb(Me_3SiCp)_2(N^{Et}, N^{Me}\text{-gnd})$, $Nb(Me_3SiCp)_2(N^{iPr}, N^{Me}\text{-gnd})$, $Nb(Me_3SiCp)_2(N^{nPr}, N^{Me}\text{-gnd})$, $Nb(Me_3SiCp)_2(N^{iBu}, N^{Me}\text{-gnd})$, $Nb(Me_3SiCp)_2(N^{nBu}, N^{Me}\text{-gnd})$, $Nb(Me_3SiCp)_2(N^{tBu}, N^{Me}\text{-gnd})$, $Nb(Me_3SiCp)_2(N^{sBu}, N^{Me}\text{-gnd})$, $Nb(Me_3SiCp)_2(N^{tAm}, N^{Me}\text{-gnd})$, $Nb(Me_3SiCp)_2(N^{TMS}, N^{Me}\text{-gnd})$, $Nb(Me_3SiCp)_2(N^{Et, tBu}, N^{Me}\text{-gnd})$, $Nb(Cp)(iPr_3Cp)(N^{Me}, N^{Me}\text{-gnd})$, $Nb(Cp)(Cp^*)(N^{Me}, N^{Me}\text{-gnd})$, $Nb(Cp)(MeCp)(N^{Et}, N^{Me}\text{-gnd})$, $Nb(Cp)(EtCp)(N^{iPr}, N^{Me}\text{-gnd})$, $Nb(Cp)(iPrCp)(N^{nPr}, N^{Me}\text{-gnd})$, $Nb(Cp)(nPrCp)(N^{iBu}, N^{Me}\text{-gnd})$, $Nb(Cp)(iBuCp)(N^{nBu}, N^{Me}\text{-gnd})$, $Nb(Cp)(tBuCp)(N^{tBu}, N^{Me}\text{-gnd})$, $Nb(Cp)(tAmCp)(N^{sBu}, N^{Me}\text{-gnd})$, $Nb(Cp)_2(N^{iPr}, N^{Me, Et}\text{-gnd})$, $Nb(Cp)_2(N^{iPr}, N^{Et}\text{-gnd})$, $Nb(Cp)_2(N^{iPr}, N^{nPr}\text{-gnd})$, $Nb(Cp)_2(N^{iPr}, N^{iPr}\text{-gnd})$, $Nb(MeCp)_2(N^{iPr}, N^{Me, Et}\text{-gnd})$, $Nb(MeCp)_2(N^{iPr}, N^{Et}\text{-gnd})$, $Nb(MeCp)_2(N^{iPr}, N^{nPr}\text{-gnd})$, $Nb(MeCp)_2(N^{iPr}, N^{iPr}\text{-gnd})$, $Nb(EtCp)_2(N^{iPr}, N^{Me, Et}\text{-gnd})$, $Nb(EtCp)_2(N^{iPr}, N^{Et}\text{-gnd})$, $Nb(EtCp)_2(N^{iPr}, N^{nPr}\text{-gnd})$, or $Nb(EtCp)_2(N^{iPr}, N^{iPr}\text{-gnd})$.

The niobium compound according to Chemical Formula 3 may be synthesized by reacting $Nb(R_5Cp)_2X_2$ with 2 equivalents of $Z(N^{R, R'}, N^{R'', R'''}\text{-gnd})$. Here, X may be selected from among halogen elements consisting of F, Cl, Br, and I; Z may be selected from among alkali metal elements consisting of Li, Na, and K; and R, R', R", and R''' may be each independently H, Me, Et, nPr, iPr, tBu, sBu, iBu, nBu, tAmyl, $SiMe_3$, $SiMe_2H$, or $SiH_2Me$. $Nb(R_5Cp)_2X_2$ may be synthesized as described in J. C. S. Dalton 1980, 180-186. $Z(N^{R, R'}, N^{R'', R'''}\text{-gnd})$ may be synthesized as described in Organometallics 2008, 27, 1596-1604. The niobium compound may be synthesized at a low temperature of −50° C. The reaction may be performed in a polar solvent, for example, THF, or diethyl ether. The niobium compound may be separated from an alkali salt by extraction using a non-polar solvent, such as pentane, hexane, cyclohexane, heptane, benzene, toluene, and the like. A result product including the synthesized niobium compound may be purified by vacuum sublimation, by vacuum distillation, or by recrystallization. The recrystallization may be performed in an appropriate solvent selected from among THF, diethyl ether, pentane, hexane, cyclohexane, heptane, benzene, toluene, and mixtures thereof.

In some embodiments, the niobium compound according to Chemical Formula 3 may be a liquid at room temperature.

According to an example embodiment, a niobium precursor composition may include the niobium compound represented by Formula (1), and impurities. The impurities may include an organic compound, a metal, or combinations thereof. In some embodiments, the impurity may include 0.01% by weight (wt %) to 2.0 wt % of an organic compound based on the total amount of the niobium precursor composition. In some other embodiments, the impurity may include 0 parts per million by weight (ppmw) to 1 ppmw of an organic compound based on the total amount of the niobium precursor composition.

The niobium compound represented by Formula (1) may be present in an amount equal to or greater than about 95 wt % (for example, about 95 wt % to about 100.0 wt %) in the niobium precursor composition. In some embodiments, the niobium compound represented by Formula (1) may be present in an amount equal to or greater than about 98 wt % (for example, about 98 wt % to about 100.0 wt %) in the niobium precursor composition. In some other embodiments, the niobium compound represented by Formula (1) may be present in an amount equal to or greater than about 99 wt % (for example, about 99 wt % to about 100.0 wt %) in the niobium precursor composition. Purity of the niobium compound represented by Formula (1) in the niobium precursor composition may be measured by proton nuclear magnetic resonance ($^1H$ NMR) or by gas or liquid chromatography coupled with a mass spectrometer.

Examples of the impurity which may be present in the niobium precursor composition may include carbodiimides, alkyl amines, dialkyl amines, alkyl imines, cyclopentadiene, dicyclopentadiene, tetrahydrofuran, ethers, pentane, cyclohexane, heptane, benzene, toluene, chlorinated metal compounds, lithium, sodium or potassium formamidinate, lithium, sodium or potassium amidinate, lithium, sodium or potassium guanidinate, lithium, sodium or potassium cyclopentadienyl, and the like. The impurity may be present in an amount equal to or less than about 5 wt % (for example, about 0.0 wt % to about 5.0 wt %) based on the total amount of the niobium precursor composition. In some embodiments, the impurity may be present in an amount equal to or less than about 2 wt % (for example, about 0.0 wt % to about 2.0 wt %) based on the total amount of the niobium precursor composition. In some other embodiments, the impurity may be present in an amount equal to or less than about 1 wt % (for example, about 0.0 wt % to about 1.0 wt %) based on the total amount of the niobium precursor composition.

The niobium precursor composition may be purified by, for example, recrystallization, by sublimation, by distillation, or by passing the gas or liquid through a suitable adsorbent, for example, a 4A molecular sieve. The niobium precursor composition may contain about 0 parts per billion by weight (ppbw) to about 1 ppmw, for example, about 0 ppbw to about 500 ppbw of a metal impurity. The metal or metalloid impurity may be aluminum (Al), arsenic (As), barium (Ba), beryllium (Be), bismuth (Bi), cadmium (Cd), calcium (Ca), chromium (Cr), cobalt (Co), copper (Cu), gallium (Ga), germanium (Ge), hafnium (Hf), zirconium (Zr), indium (In), iron (Fe), lead (Pb), lithium (Li), magnesium (Mg), manganese (Mn), tungsten (W), nickel (Ni), potassium (K), sodium (Na), strontium (Sr), thorium (Th), tin (Sn), titanium (Ti), uranium (U), zinc (Zn), etc.

The niobium precursor composition may be used as a niobium source gas for forming a niobium-containing film on a substrate. In some embodiments, the niobium precursor composition may include only the niobium compound represented by Formula (1). In some other embodiments, the niobium precursor composition may include the niobium compound represented by Formula (1), and an impurity including an organic compound, a metal, or combinations thereof.

According to an example embodiment, a method of forming a thin film may include forming a niobium-containing film on a substrate by performing a vapor deposition process while sequentially or simultaneously supplying the niobium precursor composition and a reactant onto the substrate, the niobium precursor composition including the niobium compound represented by Formula (1). For example, the niobium compound may be $Nb(MeCp)_2(N^{iPr}Me\text{-amd})$, $Nb(EtCp)_2(N^{iPr}Me\text{-amd})$, or $Nb(iPrCp)_2(N^{iPr}Me\text{-amd})$, and the reactant may be $NH_3$. In some embodiments, the niobium compound may be a liquid at room temperature. The forming of the niobium-containing film may be performed at a temperature of about 100° C. to about 600° C. and at a pressure of about 1 Pa to about $10^5$ Pa.

The method of forming the thin film using the niobium precursor composition may be useful for fabricating semiconductor, photovoltaic, LCD-TFT, or planar-type devices. The niobium compound constituting the niobium precursor composition may be obtained using various deposition methods known in the art, and may be usefully used for forming a niobium nitride thin film.

Examples of a vapor deposition method suitable for forming a thin film using the niobium precursor composition including the niobium compound may include a chemical vapor deposition (CVD) method and an atomic layer deposition (ALD) method. Examples of the CVD method may include thermal CVD, plasma enhanced CVD (PECVD), pulsed CVD (PCVD), low pressure CVD (LPCVD), sub-atmospheric CVD (SACVD) or atmospheric pressure CVD (APCVD), hot-wire CVD (HWCVD, also referred to as cat-CVD, in which a hot wire serves as an energy source for the deposition process), radical incorporated CVD, and combinations thereof). Examples of the ALD method may include thermal ALD, plasma enhanced ALD (PEALD), spatial ALD, hot-wire ALD (HWALD), radical incorporated ALD, and combinations thereof. Supercritical fluid deposition may also be used. Among the various examples of the deposition method set forth above, ALD, PEALD, spatial ALD, or the like may be used in order to provide good step coverage and control a film thickness.

According to the method of forming the thin film, to form the niobium-containing film by a CVD method, the niobium precursor composition, which includes the niobium compound represented by Formula (1), and the reactant may be simultaneously supplied onto the substrate. In some embodiments, while the niobium precursor composition and the reactant are simultaneously supplied onto the substrate, at least one of the niobium precursor composition and the reactant may be plasma-treated.

According to the method of forming the thin film, to form the niobium-containing film by an ALD method, the forming of the niobium-containing film may include vaporizing the niobium precursor composition, which includes the niobium compound represented by Formula (1), forming a Nb source adsorption layer on the substrate by supplying the vaporized niobium precursor composition onto the substrate, and supplying the reactant onto the Nb source adsorption layer. In some embodiments, before the supplying of the vaporized niobium precursor composition onto the substrate, the forming of the niobium-containing film may further include plasma-treating the vaporized niobium precursor composition. In some other embodiments, before the supplying of the reactant onto the Nb source adsorption layer, the forming of the niobium-containing film may further include plasma-treating the reactant.

In the forming of the niobium-containing film according to the method of forming the thin film, the niobium compound used as a niobium precursor may be supplied as a neat niobium compound, or as a blended niobium compound with a suitable solvent. The solvent may include ethyl benzene, xylene, mesitylene, decalin, decane, dodecane, or the like. The niobium compound may be present in various concentrations in the solvent.

The niobium precursor composition including the neat or blended niobium compound may be introduced into a reactor in the form of vapor by using a heated container, a gas line, a liquid mass flow controller (LMFC), a vaporizer, or the like. To make the niobium precursor composition into the form of vapor, the niobium precursor composition including the neat or blended niobium compound may be vaporized by heating, by bubbling, or by using a vaporizer.

The niobium precursor composition including the neat or blended niobium compound may be supplied in a liquid state to a vaporizing device. In some embodiments, the niobium precursor composition may be vaporized before introduced into the reactor. In some embodiments, the niobium precursor composition including the neat or blended niobium compound may be vaporized by passing a carrier gas into a container containing the composition, or by bubbling the carrier gas into the composition. The carrier gas may include Ar, He, $N_2$, mixtures thereof, etc. Dissolved oxygen, which may be present in the niobium precursor composition including the neat or blended niobium compound, may be removed by bubbling using the carrier gas. As such, after the dissolved oxygen is removed, the carrier gas and the niobium precursor composition may be introduced into the reactor as a vapor.

The container containing the niobium precursor composition may be heated to a temperature that allows the niobium precursor composition to be present in a liquid state and to have a sufficient vapor pressure. For example, the container may be maintained at a temperature of about 0° C.

to about 150° C. The temperature of the container may be controlled to control an amount of the vaporized niobium precursor. For example, the reactor may include a parallel-plate type reactor, a cold-wall type reactor, a hot-wall type reactor, a single-wafer reactor, a multi-wafer reactor, or a deposition system providing suitable conditions for reaction of a compound and formation of a thin film. These reactors or deposition systems may be used for ALD or CVD deposition processes.

The reactor may simultaneously handle one or more substrates during the deposition process. The substrate may be any suitable substrate used for fabricating semiconductor, photovoltaic, planar-type, or LCD-TFT devices. For example, the substrate may include a silicon, silica, glass, or GaAs wafer. The wafer may include one or more layers of different materials, which are deposited in a previous fabrication process before formation of the niobium-containing film, for example, a niobium nitride thin film. For example, the wafer may include a (crystalline, amorphous, porous, or the like) silicon layer, a silicon oxide layer, a silicon nitride layer, a silicon oxynitride layer, a carbon-doped silicon oxide (SiCOH) layer, or combinations thereof. The wafer may include a metal or metal nitride layer (for example, copper, tungsten, titanium nitride, or the like) or a noble metal layer (for example, platinum, palladium, rhodium, or gold). The wafer may include manganese, manganese oxide, or the like. In addition, the wafer may include a polymer layer such as poly(3,4-ethylenedioxythiophene):poly(styrenesulfonate) [PEDOT:PSS] or the like. The layers set forth above as examples may be planar or patterned on the wafer.

In the method of forming the thin film according to some embodiments, the niobium nitride thin film may be directly deposited on the wafer, or may be directly deposited on one layer or a plurality of layers among layers on an upper side of the wafer. As used herein, the term "film" or "layer" refers to a material which has a thickness and is placed or deposited on a certain surface, and the surface may be an upper side of a specific pattern such as a trench, a line, or the like. Throughout the specification and claims, the wafer and layers formed thereon are referred to as the substrate. For example, a first niobium nitride film may be deposited on a Si layer. In a subsequent process, a zirconium oxide layer may be deposited on the first niobium nitride film, and a second niobium nitride film may be deposited on the zirconium oxide layer, thereby forming a NbN/ZrO$_2$/NbN stacked structure used for DRAM capacitors.

The temperature and pressure inside the reactor may be maintained under conditions that are suitable for vapor deposition. That is, after the vaporized niobium precursor is injected into a chamber, conditions inside the chamber are conditions that allow at least a portion of the niobium precursor to be deposited on the substrate to form a niobium nitride film. The pressure inside the reactor may be maintained at about 1 Pa to about 10$^5$ Pa, for example, about 25 Pa to about 10$^3$ Pa, as suitable for deposition parameters. The temperature inside the reactor may be maintained at about 100° C. to about 500° C., for example, about 150° C. to about 400° C. Herein, the expression "at least a portion of the precursor is deposited" may be used for explaining that some or all of the precursor reacts with or is adsorbed onto the substrate.

The temperature of the reactor may be controlled by controlling a temperature of a heating device, such as a stage heater, a lamp, and the like, in the chamber, or by controlling a temperature of a reactor wall. The reactor wall may be heated to a temperature suitable for depositing a desired-quality film which has a desired physical state and composition. The temperature to which the reactor wall can be heated may range from, for example, about 100° C. to about 500° C. When a plasma deposition process is used, a deposition temperature may be selected from a range from about 150° C. to about 400° C.

In the method of forming the thin film, the reactant may be introduced into the reactor together with the niobium precursor composition. The reactant may include N$_2$, NH$_3$, N$_2$H$_4$, N(SiH$_3$)$_3$, N(CH$_3$)H$_2$, N(C$_2$H$_5$)H$_2$, N(CH$_3$)$_2$H, N(C$_2$H$_5$)$_2$H, N(CH$_3$)$_3$, N(C$_2$H$_5$)$_3$, (SiMe$_3$)$_2$NH, (CH$_3$)HNNH$_2$, (CH$_3$)$_2$NNH$_2$, phenylhydrazine, pyrazoline, radicals thereof, and mixtures thereof.

The reactant may be treated with plasma so as to be decomposed into a radical form. When the reactant is treated with plasma, N$_2$ may be used as a gas for nitridation. For example, the plasma may be generated with a power ranging from about 50 W to about 500 W, for example, from about 100 W to about 400 W. The plasma may be generated or present inside the reactor itself. The plasma may be formed by a plasma generating system outside the chamber.

In the method of forming the thin film, to form the plasma-treated reactant as the reactant introduced into the reactor together with the niobium precursor composition, a direct plasma manner in which plasma is generated inside the reaction chamber may be applied. The reactant may be injected into the reaction chamber before plasma treatment thereof, or may be injected simultaneously with plasma treatment thereof. In-situ plasma may be, for example, 13.65 MHz RF inductively coupled plasma that is generated between a shower head and a substrate holder. The substrate or the shower head may be an electrode supplied with power depending upon whether a positive ion effect occurs. Applied power in an in-situ plasma generator may range from about 30 W to about 1000 W. In some embodiments, the applied power may range from about 30 W to about 600 W. In some other embodiments, the applied power may range from about 100 W to about 500 W.

In some embodiments, the plasma-treated reactant may be formed outside the reaction chamber. For this purpose, remote plasma may be generated with a power of, for example, about 1 kW to about 10 kW or about 2.5 kW to about 7.5 kW.

Depending upon desired properties of a film intended to be formed on the substrate, an additional precursor may be injected into the reactor. The additional precursor may be used to provide an additional element to the niobium nitride film. The additional element may include lanthanides (ytterbium, erbium, dysprosium, gadolinium, praseodymium, cerium, lanthanum, yttrium), zirconium, germanium, silicon, magnesium, titanium, manganese, ruthenium, bismuth, lead, aluminum, or mixtures thereof. When the additional precursor is used, a film deposited on the substrate may contain the niobium metal together with the additional element.

In the method of forming the thin film, the niobium precursor composition for forming the niobium nitride film, and the reactant may be introduced into the reactor simultaneously (chemical vapor deposition), sequentially (atomic layer deposition), or in other manners obtained by combinations thereof. In some embodiments, the method of forming the thin film may include purging the reactor with an inert gas between the injecting of the niobium precursor composition and the injecting of the reactant. In other embodiments, the reactant and the niobium precursor composition are injected together into the reactor, and mixed in the reactor. In further embodiments, the reactant may be continuously injected, and the niobium precursor composition may be injected in a pulsed manner (pulsed chemical vapor deposition).

In some embodiments, the vaporized niobium precursor composition and the reactant may be sequentially or simultaneously injected into the reactor in a pulsed manner (for example, pulsed CVD). Each pulse of the niobium precursor composition may last for a time period of about 0.01 seconds to about 10 seconds, for example, about 0.3 seconds to about 3 seconds, or about 0.5 seconds to about 2 seconds. In some other embodiments, the reactant may be introduced into the reactor in a pulsed manner. In these embodiments, each pulse may last for a time period of about 0.01 seconds to about 10 seconds, for example, about 0.3 seconds to about 3 seconds, or about 0.5 seconds to about 2 seconds. In some further embodiments, the niobium precursor composition and the reactant may be simultaneously sprayed from a shower head under the condition that a susceptor securing a plurality of wafers is rotated (spatial ALD).

In the method of forming the thin film, the deposition time may vary with specific process parameters. The deposition time may continue as long as needed to form a film having required properties. In the method of forming the thin film, the formed thin film may have a thickness varying from several angstroms (Å) to several hundreds of micrometers (μm), depending upon specific deposition processes. The deposition process may be performed as many times as needed to obtain a desired film.

In the method of forming the thin film according to some embodiments, a CVD process may be performed as follows. First, the niobium precursor composition for forming the niobium nitride film, and the reactant may be simultaneously injected into the reactor. The niobium precursor composition reacts with the reactant, thereby obtaining the niobium nitride film. When plasma is used in the CVD process, the CVD process may be a PECVD process. The reactant may be treated with plasma before or after introduced into the chamber.

In the method of forming the thin film according to some embodiments, a first ALD process may be performed as follows. First, the niobium precursor composition may be injected into the reactor and chemically adsorbed onto the substrate (a first process). An excess of the niobium precursor composition may be removed from the reactor by purging or pumping the reactor. The reactant (for example, $NH_3$) may be injected into the reactor and react with the niobium precursor composition, which is chemically adsorbed onto the substrate, in a self-limiting manner (a second process). An excess of the reactant may be removed from the reactor by purging or pumping the reactor. If a film intended to be formed is a niobium nitride film, a two-stage process including the first and second processes as set forth above may be repeated until the film having a desired or required thickness is obtained.

If the film be formed is to contain niobium and a second element, then, after the two-stage process, an additional precursor including the second element may be injected into the reactor (a third process). The additional precursor may be selected based on properties of the niobium nitride film that is deposited. After being injected into the reactor, the additional precursor may contact the substrate. An excess of the additional precursor may be removed from the reactor by purging or pumping the reactor. Next, the reactant may be injected into the reactor again to react with the additional precursor (a fourth process). An excess of the reactant may be removed from the reactor by purging or pumping the reactor. When the film having a desired thickness is deposited, the process may be completed. For a thicker film, a four-stage process including the first to fourth processes as set forth above may be repeated. By changing the supply of the niobium precursor composition for forming the niobium nitride film, the additional precursor, and the reactant, a film having desired composition and thickness may be deposited.

In the ALD process described above, if the reactant is treated with plasma, the ALD process may be a PEALD process. The reactant may be treated with plasma before or after being injected into the chamber.

In the method of forming the thin film according to some other embodiments, a second ALD process may be performed as follows. First, one of the niobium precursor compositions according to an example embodiment, for example, niobium bis(ethylcyclopentadienyl) diisopropylamidinate ($Nb(EtCp)_2(N^{iPr}\text{Me-amd})$), may be introduced into the reactor in a vapor phase, and may contact a Si substrate. Next, an excess of the composition may be removed from the reactor by purging or pumping the reactor. Next, the reactant (for example, $NH_3$) may be injected into the reactor, and react with the niobium precursor composition, which is present on a surface of the substrate, in a self-limiting manner, thereby forming the niobium nitride film. An excess of the reactant (for example, $NH_3$ gas) may be removed from the reactor by purging or pumping the reactor. The two-stage process set forth above may be repeated until a first niobium nitride film (first NbN film) having a desired thickness, for example, a thickness of 10 Å, is obtained.

Next, a $ZrO_2$ film may be formed on the first NbN film. Here, $ZrCp(NMe_2)_3$ may be used as a Zr precursor.

Next, a second NbN film may be formed on the $ZrO_2$ film by repeating the second ALD process set forth above using $Nb(EtCp)_2(N^{iPr}\text{Me-amd})$ and $NH_3$. As a result, an obtained $NbN/ZrO_2/NbN$ stacked structure may be used for DRAM capacitors.

When a niobium-containing film (for example, a NbN film) having a desired thickness is obtained, the niobium-containing film may be subjected to an additional post-treatment, for example, high-temperature thermal annealing, furnace annealing, high-temperature rapid thermal annealing, UV or e-beam curing, and/or plasma gas exposure. For example, to post-treat the NbN film, the NbN film may be exposed to an inert atmosphere, a N-containing atmosphere, or combinations thereof at a temperature of about 200° C. to about 1,000° C. for a time period of about 0.1 seconds to about 7,200 seconds. In some embodiments, the NbN film may be post-treated at a temperature of about 400° C. for about 3,600 seconds in an inert atmosphere or a N-containing atmosphere.

The niobium-containing film formed by the method of forming the thin film according to embodiments may contain little or a relatively low amount of impurities, and thus have an improved density, thereby providing an effect of improving leakage current.

In some embodiments, the annealing of the niobium-containing film may be performed in the same reaction chamber in which the deposition process is performed.

In some other embodiments, after the deposition process is performed, the substrate is taken out from the reaction chamber, and may be subjected to an annealing/flash annealing process in a separate apparatus. For example, high-temperature thermal annealing is performed as a post-treatment process of the NbN film, thereby reducing carbon and nitrogen contamination of the NbN film. This can contribute to improving resistivity of the NbN film.

After post-treatment of the NbN film by annealing, the NbN film may have a bulk resistivity of about 50 µΩ·cm to about 1,000 µΩ·cm at room temperature. Room temperature may range from about 20° C. to about 28° C. depending upon the seasons. Bulk resistivity is also known as volume resistivity. The bulk resistivity of the NbN film may be measured on the NbN film having a thickness of about 50 nm at room temperature.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Example 1—Synthesis of bis-cyclopentadienyl diisopropylacetamidinato niobium ($NbCp_2(N^{iPr}$ Me-amd))

Methyl lithium (MeLi, 10 mL, 16 mmol) was slowly added dropwise to a solution in which diisopropyl carbodiimide (2.0 g, 16 mmol) was dissolved in about 20 mL of tetrahydrofuran (THF) cooled to −78° C. The components were stirred at room temperature for 3 hours, followed by adding the mixture to a solution in which $Nb(Cp)_2(Cl)_2$ (2.32 g, 7.9 mmol) was dissolved in about 20 mL of THF at −78° C. The mixture was stirred overnight at room temperature. Next, the solvent was removed in a vacuum, and the product was extracted with toluene, thereby obtaining a black solid material. The obtained material was purified by sublimation at 190° C. at 20 mTorr, thereby obtaining 1.08 g (37%) of a pure black solid material.

FIG. 1 is a $^1$H-NMR spectrum of the material obtained in Example 1.

$^1$H-NMR (δ, ppm, C6D6): 4.90 (s, 8H), 2.97 (m, 2H), 1.17 (s, 3H), 0.75 (d, 12H).

Figure 2:
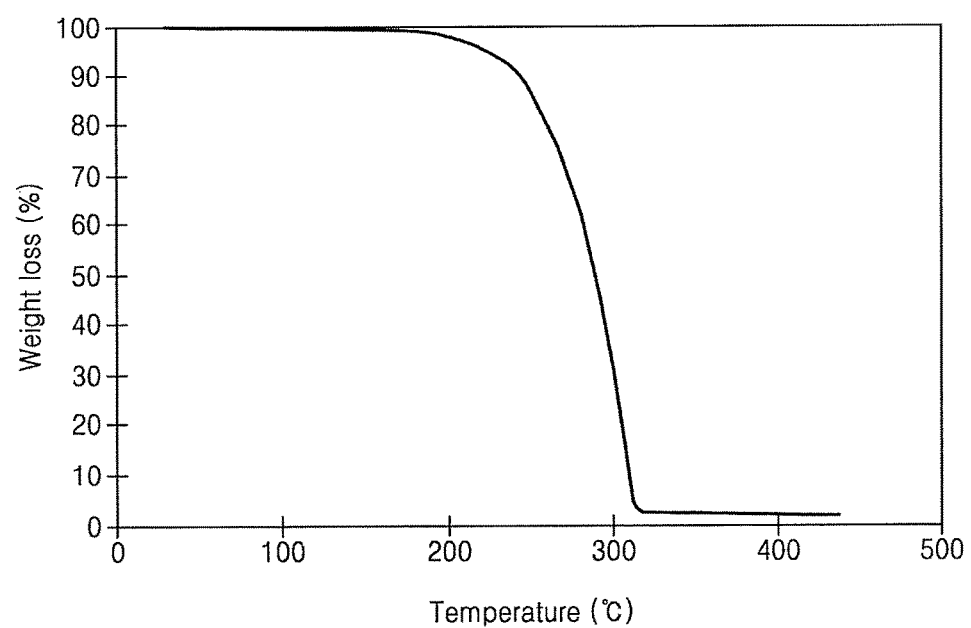
FIG. 2 illustrates a thermogravimetric analysis (TGA) graph depicting the percentage of weight loss with increasing temperature of $NbCp_2(N^{iPr}$ Me-amd)

The solid material obtained in Example 1 was subjected to Open-Cup thermogravimetric analysis (TGA) at a heating rate of 10° C./min in an atmosphere of nitrogen flowing at 200 mL/min. As a result, the remaining mass of the solid material was 1.7% (15% in the case of Close-Cup). These results are shown in FIG. 2. A TGA graph of FIG. 2 shows the percentage of weight loss with increasing temperature of the material.

Example 2—Synthesis of bis-cyclopentadienyl diisopropylvaleramidinato niobium ($NbCp_2(N^{iPr}$ nBu-amd))

Butyl lithium (nBuLi, 250 mL, 0.4 mol) was slowly added dropwise to a solution in which diisopropyl carbodiimide (50.5 g, 0.4 mol) was dissolved in about 200 mL of THF at −78° C. The components were stirred at room temperature for 12 hours, followed by adding the mixture to a solution in which $Nb(Cp)_2(Cl)_2$ (58.8 g, 0.2 mol) was dissolved in about 200 mL of THF at −78° C. The mixture was stirred overnight at room temperature. Next, the solvent was removed in a vacuum, and the product was extracted with toluene, thereby obtaining a black solid material. The obtained material was purified through sublimation at 150° C. at 10 mTorr, thereby obtaining 37.85 g (46%) of a pure black solid material.

Figure 3:
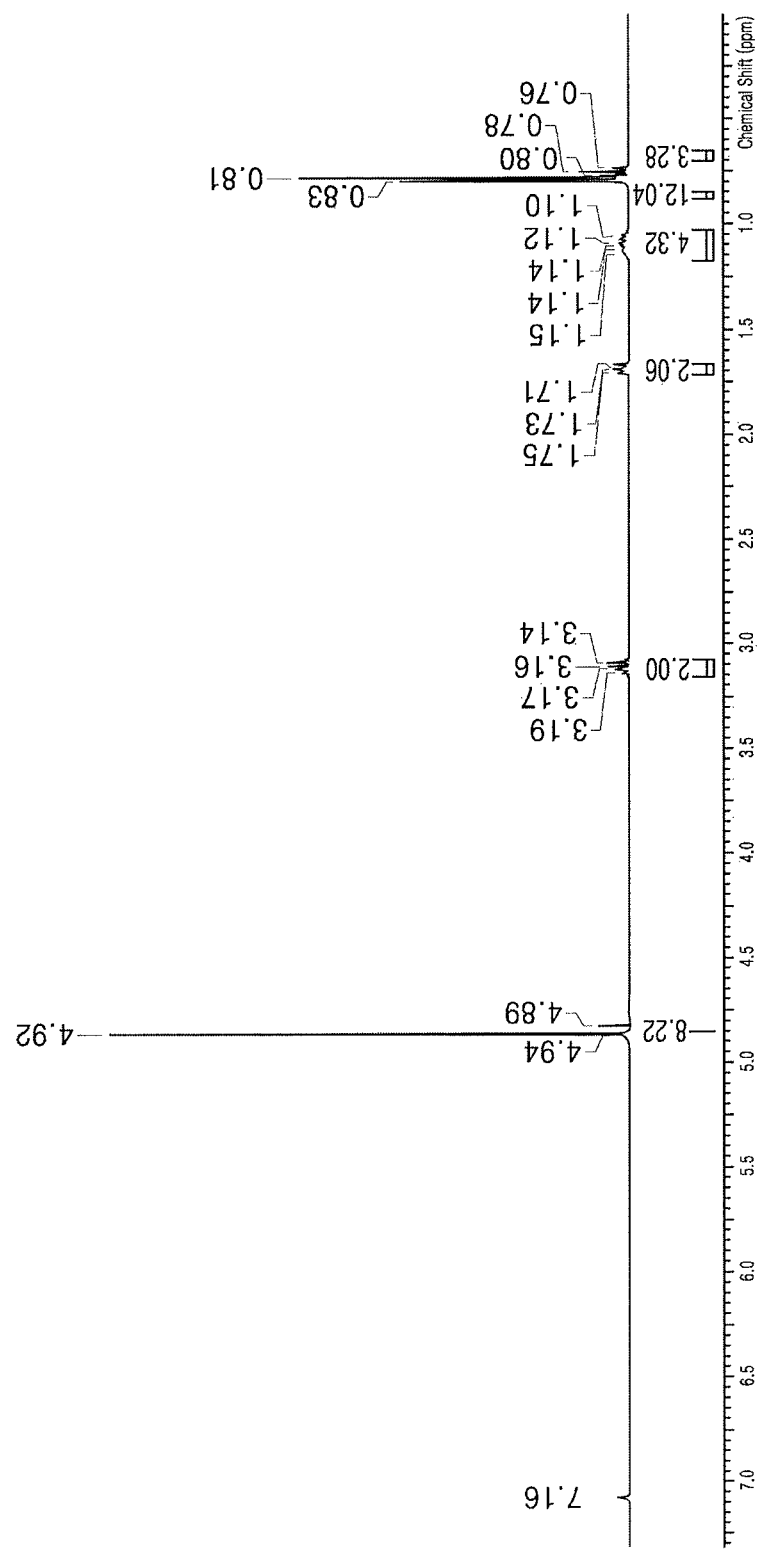
FIG. 3 illustrates a $^1$H-NMR spectrum of bis-cyclopentadienyl diisopropylvaleramidinato niobium ($NbCp_2(N^{iPr}$ nBu-amd))

FIG. 3 is a $^1$H-NMR spectrum of the material obtained in Example 2. $^1$H-NMR (δ, ppm, C6D6): 4.92 (s, 8H), 3.16 (m, 2H), 1.73 (m, 2H), 1.13 (m, 4H), 0.81 (d, 12H), 0.78 (t, 3H).

Figure 4:
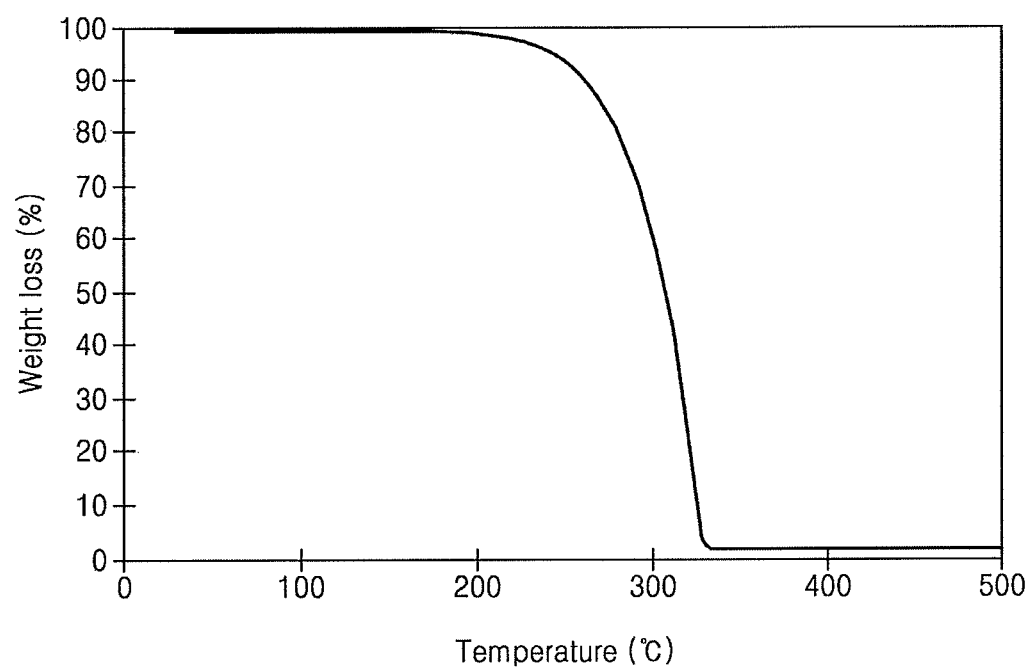
FIG. 4 illustrates a TGA graph depicting the percentage of weight loss with increasing temperature of $NbCp_2(N^{iPr}$ nBu-amd)

The solid material obtained in Example 2 was subjected to Open-Cup thermogravimetric analysis (TGA) at a heating rate of 10° C./min in an atmosphere of nitrogen flowing at 200 mL/min. As a result, the remaining mass of the solid material was 1.7% (22% in the case of Close-Cup). These results are shown in FIG. 4. A TGA graph of FIG. 4 shows the percentage of weight loss with increasing temperature of the material.

Example 3—Formation of NbN Thin Film (1)

A NbN thin film was formed using $NbCp_2(N^{iPr}$ nBu-amd) synthesized in Example 2. For this purpose, pyrolysis characteristics of a $NbCp_2(N^{iPr}$ nBu-amd) precursor itself were evaluated using the $NbCp_2(N^{iPr}$ nBu-amd) precursor contained in a container heated up to 155° C., and ALD deposition characteristics were evaluated using the precursor and ammonia corresponding to a co-reactant.

A pyrolysis test was performed under the condition of a reactor pressure fixed at 0.5 Torr by flowing a vapor of $NbCp_2(N^{iPr}$ nBu-amd) on a silicon wafer without the co-reactant for a given time period.

Figure 5:
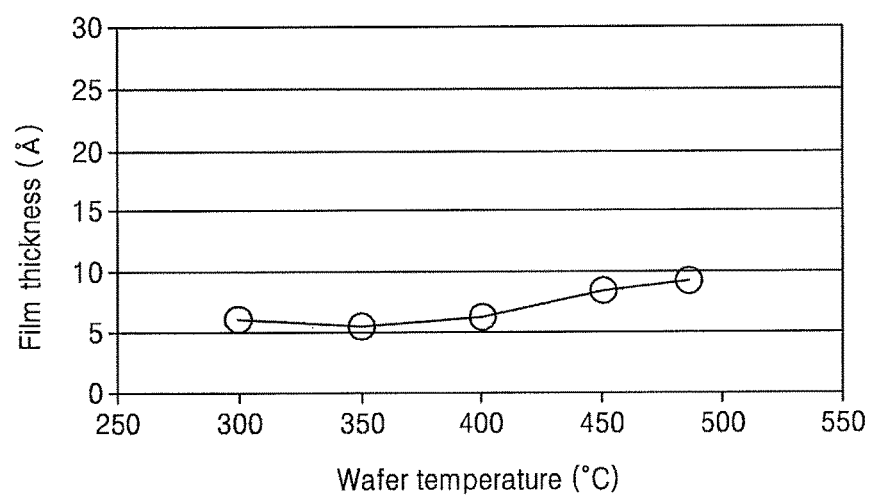
FIG. 5 illustrates a graph depicting a deposition rate of a thin film using $NbCp_2(N^{iPr}$ nBu-amd) without a reactant at a temperature of 300° C. to 450° C.

FIG. 5 shows a deposition rate of a thin film deposited at a temperature of 300° C. to 450° C. using $NbCp_2(N^{iPr}$ nBu-amd) without the co-reactant. From FIG. 5, it can be seen that since the thickness of the thin film did not increase up to about 400° C., the thin film was thought not to be deposited up to about 400° C., and thermal stability of $NbCp_2(N^{iPr}$ nBu-amd) was excellent up to about 400° C. The thickness of the thin film increased at a temperature of about 400° C. or more, and it was understood that the reason for this was that a small amount of a material was deposited on the silicon wafer due to the occurrence of thermal self decomposition of the precursor.

A thin film deposition process was performed according to typical ALD conditions using a reactor fixed at about 2 Torr and using ammonia as the co-reactant. ALD behaviors having complete surface saturation on a pure silicon wafer at 350° C. were confirmed.

Figure 6:
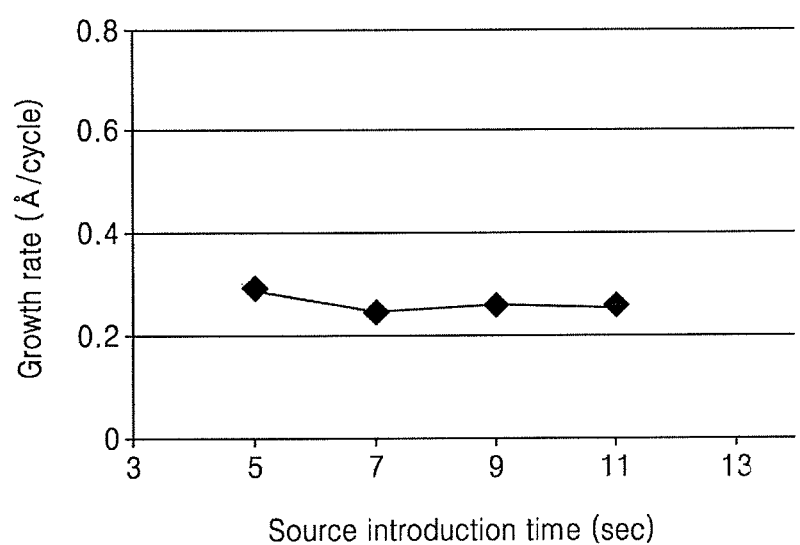
FIG. 6 illustrates a graph depicting a growth rate of a NbN thin film according to supply time of a $NbCp_2(N^{iPr}$ nBu-amd) precursor at 350° C.

FIG. 6 is a graph depicting a growth rate of a NbN thin film according to supply time of a $NbCp_2(N^{iPr}$ nBu-amd) precursor at 350° C. when the NbN thin film is formed according to Example 3 using the $NbCp_2(N^{iPr}$ nBu-amd) precursor. From FIG. 6, it can be seen that a deposition rate of the NbN thin film was stably constant at about 0.26 Å/cycle with increasing the injection time of the precursor.

Figure 7:
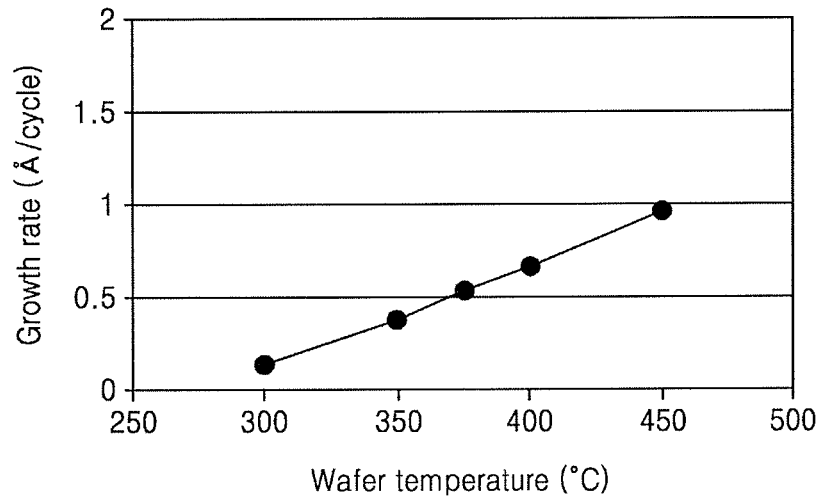
FIG. 7 illustrates a graph depicting a growth rate of a NbN thin film according to a chamber temperature when the NbN thin film is formed using $NbCp_2(N^{iPr}$ nBu-amd)

FIG. 7 is a graph depicting a growth rate of a NbN thin film according to a chamber temperature when the NbN thin film is formed according to Example 3 using a $NbCp_2(N^{iPr}$ nBu-amd) precursor. For evaluation of FIG. 7, the growth rate of the NbN thin film was measured from 300° C. to 450° C. From FIG. 7, it can be seen that the growth rate of the NbN thin film ranged from 0.2 Å/cycle to 0.6 Å/cycle at 300° C. to 400° C.

Figure 8:
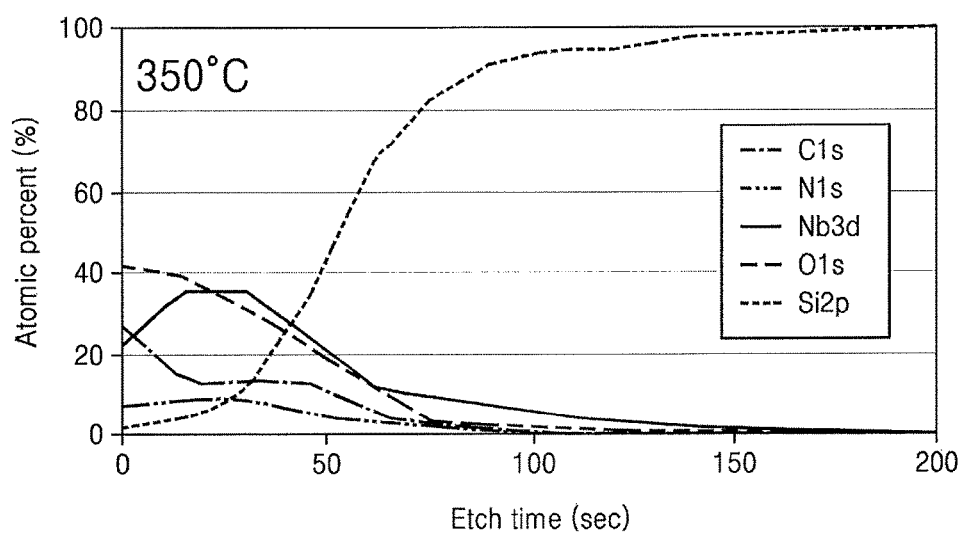
FIG. 8 illustrates a graph showing a result of X-ray photoelectron spectroscopy (XPS) analysis of a thin film deposited at 350° C. using $NbCp_2(N^{iPr}$ nBu-amd)
Figure 9:
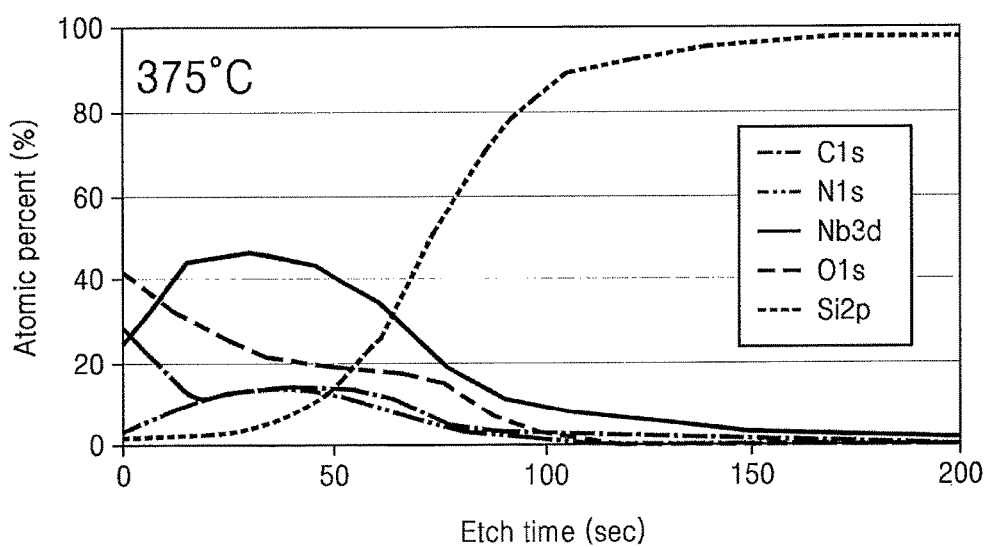
FIG. 9 illustrates a graph showing a result of XPS analysis of a thin film deposited at 375° C. using $NbCp_2(N^{iPr}$ nBu-amd)

FIGS. 8 and 9 are graphs respectively showing results of X-ray photoelectron spectroscopy (XPS) analysis of thin films deposited at 350° C. and 375° C. according to Example 3.

Example 4—Synthesis of bis-methylcyclopentadienyl diisopropylacetamidinato niobium ($Nb(MeCp)_2$ ($N^{iPr}$ Me-amd))

Methyl lithium (7.4 mL, 11.9 mmol) was slowly added dropwise to a solution in which diisopropyl carbodiimide (1.5 g, 11.9 mmol) was dissolved in about 20 mL of THF at −78° C. The components were stirred at room temperature for 3 hours, followed by adding the mixture to a solution in which Nb(MeCp)$_2$(Cl)$_2$ (2.32 g, 5.9 mmol) was dissolved in about 20 mL of THF at −78° C. The mixture was stirred overnight at room temperature. Next, the solvent was removed in a vacuum, and the product was extracted with toluene, thereby obtaining a black liquid. The obtained liquid was purified by distillation at 220° C. at 20 mTorr (distillation apparatus temperature: 84° C.), thereby obtaining 0.80 g (34%) of a pure black wax-like solid material.

Figure 10:
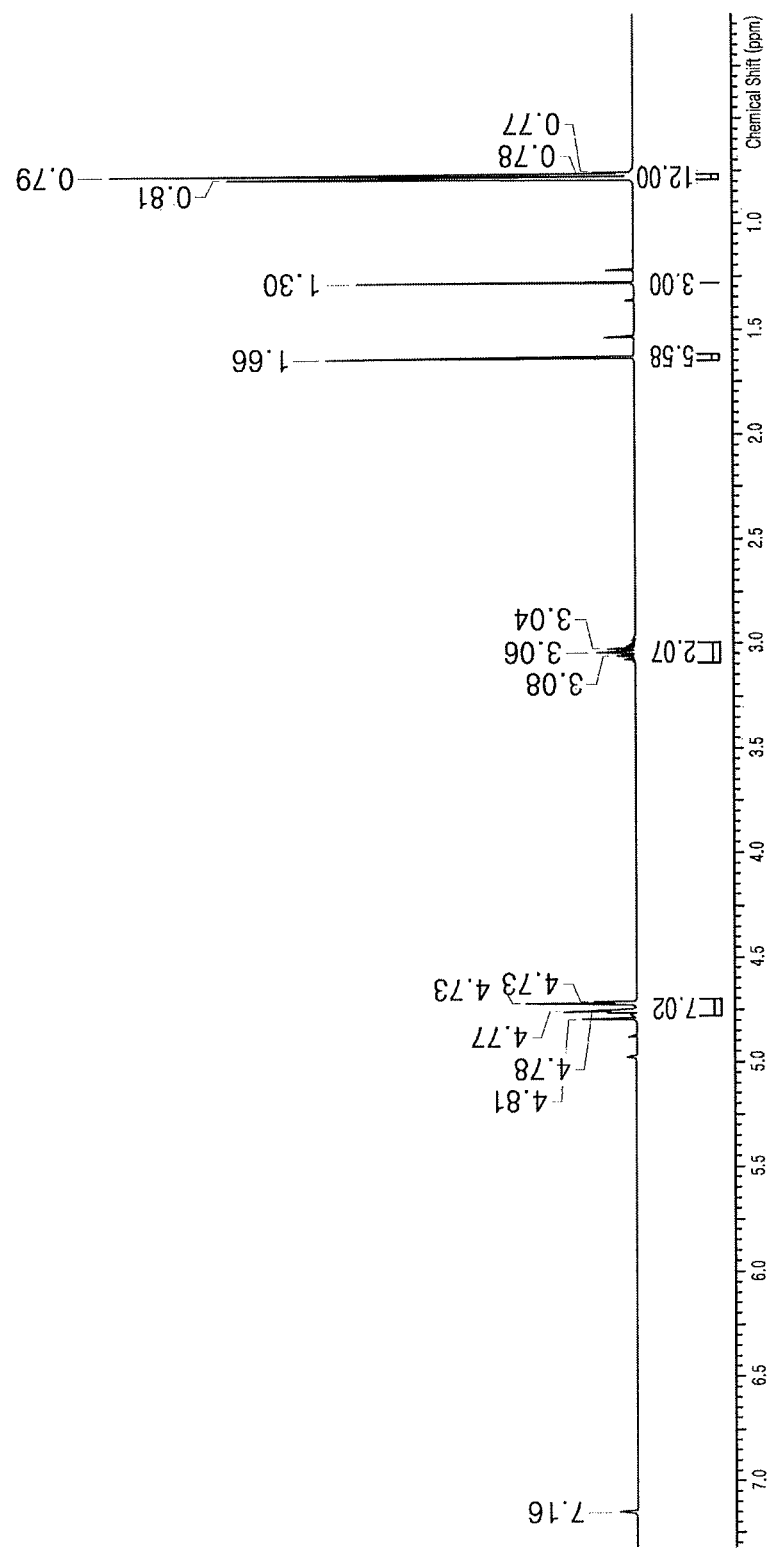
FIG. 10 illustrates a $^1$H-NMR spectrum of bis-methylcyclopentadienyl diisopropylacetamidinato niobium (Nb$(MeCp)_2(N^{iPr}$ Me-amd))

FIG. 10 is a $^1$H-NMR spectrum of the material obtained in Example 4. $^1$H-NMR (δ, ppm, C6D6): 4.73-4.78 (m, 8H), 3.06 (m, 2H), 1.66 (s, 6H), 1.30 (s, 3H), 0.79 (d, 12H).

Figure 11:
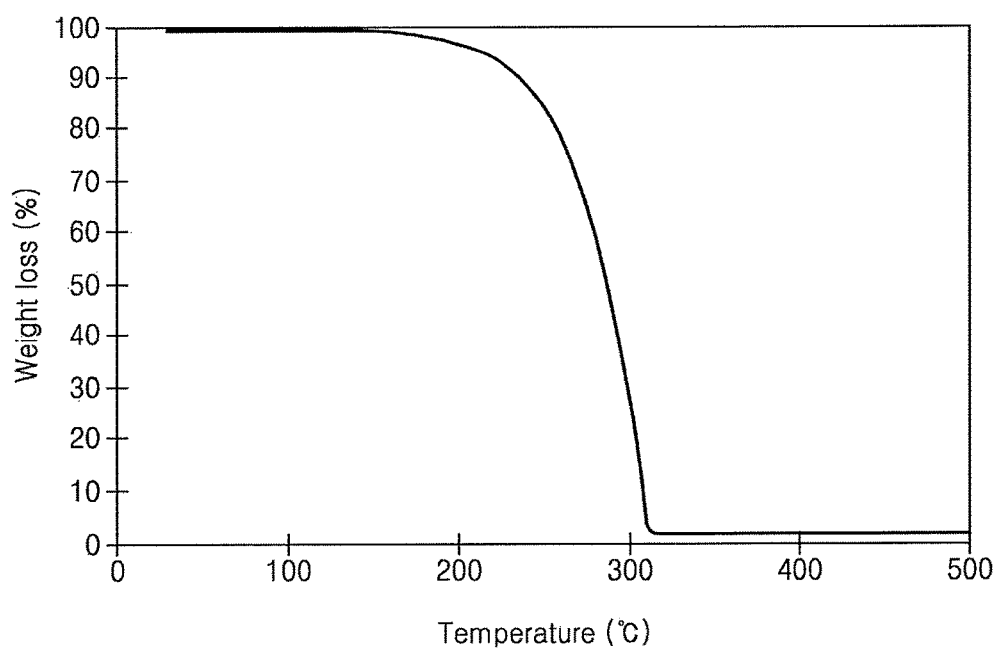
FIG. 11 illustrates a TGA graph depicting the percentage of weight loss with increasing temperature of $Nb(MeCp)_2$ ($N^{iPr}$ Me-amd)

The solid material obtained in Example 4 was subjected to Open-Cup thermogravimetric analysis at a heating rate of 10° C./min in an atmosphere of nitrogen flowing at 200 mL/min. As a result, the remaining mass of the solid material was 1.7% (17% in the case of Close-Cup). These results are shown in FIG. 11. A TGA graph of FIG. 11 shows the percentage of weight loss with increasing temperature of the material.

Example 5—Synthesis of bis-methylcyclopentadienyl diisopropylvaleramidinato niobium (Nb (MeCp)$_2$ (N$^{iPr}$ nBu-amd))

Butyl lithium (7.4 mL, 11.9 mmol) was slowly added dropwise to a solution in which diisopropyl carbodiimide (1.5 g, 11.9 mmol) was dissolved in about 20 mL of THF at −78° C. The components were stirred at room temperature for 3 hours, followed by adding the mixture to a solution in which Nb(MeCp)$_2$(Cl)$_2$ (2.32 g, 5.9 mmol) was dissolved in about 20 mL of THF at −78° C. The mixture was stirred overnight at room temperature. Next, the solvent was removed in a vacuum, and the product was extracted with toluene, thereby obtaining a black liquid. The obtained material was purified by vacuum distillation at 210° C. at 30 mTorr (distillation apparatus temperature: 60° C.), thereby obtaining a black liquid.

Figure 12:
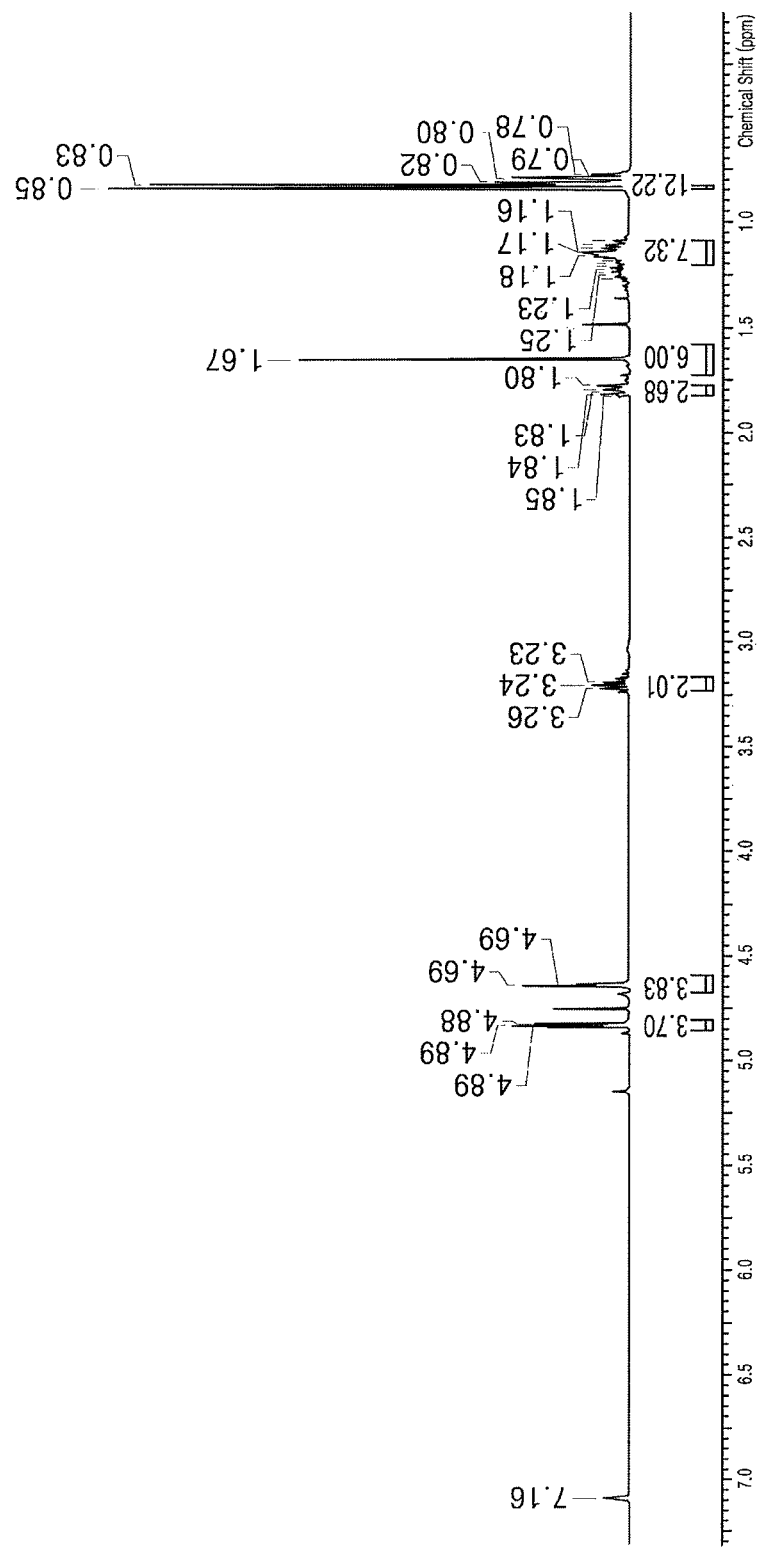
FIG. 12 illustrates a $^1$H-NMR spectrum of bis-methylcyclopentadienyl diisopropylvaleramidinato niobium (Nb$(MeCp)_2(N^{iPr}$ nBu-amd))

FIG. 12 is a $^1$H-NMR spectrum of the material obtained in Example 5. $^1$H-NMR (δ, ppm, C6D6): 4.69-4.89 (m, 8H), 3.24 (m, 2H), 1.81 (m, 2H), 1.67 (s, 6H), 1.17 (m, 4H), 0.83 (d, 12H), 0.80 (t, 3H).

Figure 13:
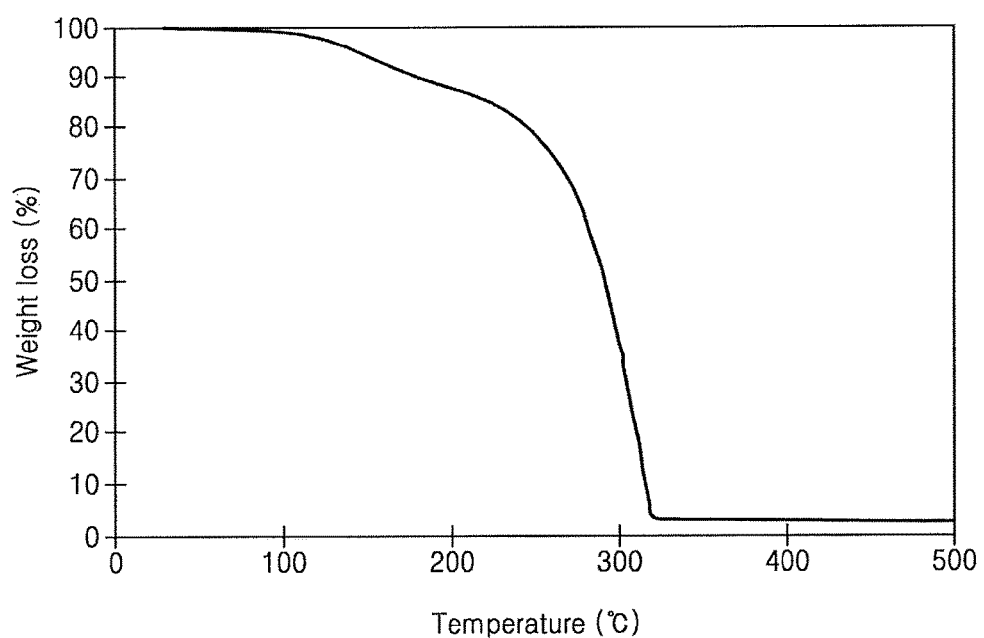
FIG. 13 illustrates a TGA graph depicting the percentage of weight loss with increasing temperature of $Nb(MeCp)_2$ ($N^{iPr}$ nBu-amd)

The material obtained in Example 5 was subjected to Open-Cup thermogravimetric analysis at a heating rate of 10° C./min in an atmosphere of nitrogen flowing at 200 mL/min. As a result, the remaining mass of the material was 2.7% (24% in the case of Close-Cup). These results are shown in FIG. 13. A TGA graph of FIG. 13 shows the percentage of weight loss with increasing temperature of the material.

Example 6—Synthesis of bis-methylcyclopentadienyl t-butyl, ethylacetamidinato niobium (Nb (MeCp)$_2$(N$^{tBu, Et}$ Me-amd))

Methyl lithium (7.4 mL, 11.9 mmol) was slowly added dropwise to a solution in which n-butylethyl carbodiimide (1.5 g, 11.9 mmol) was dissolved in about 20 mL of THF at −78° C. The components were stirred at room temperature for 3 hours, followed by adding the mixture to a solution in which Nb(MeCp)$_2$(Cl)$_2$ (2.32 g, 5.9 mmol) was dissolved in about 20 mL of THF at −78° C. The mixture was stirred overnight at room temperature. Next, the solvent was removed in a vacuum, and the product was extracted with toluene, thereby obtaining a black wax-like solid material. The obtained material was purified by vacuum distillation at 200° C. at 20 mTorr (distillation apparatus temperature: 106° C.), thereby obtaining a black wax-like solid material.

Figure 14:
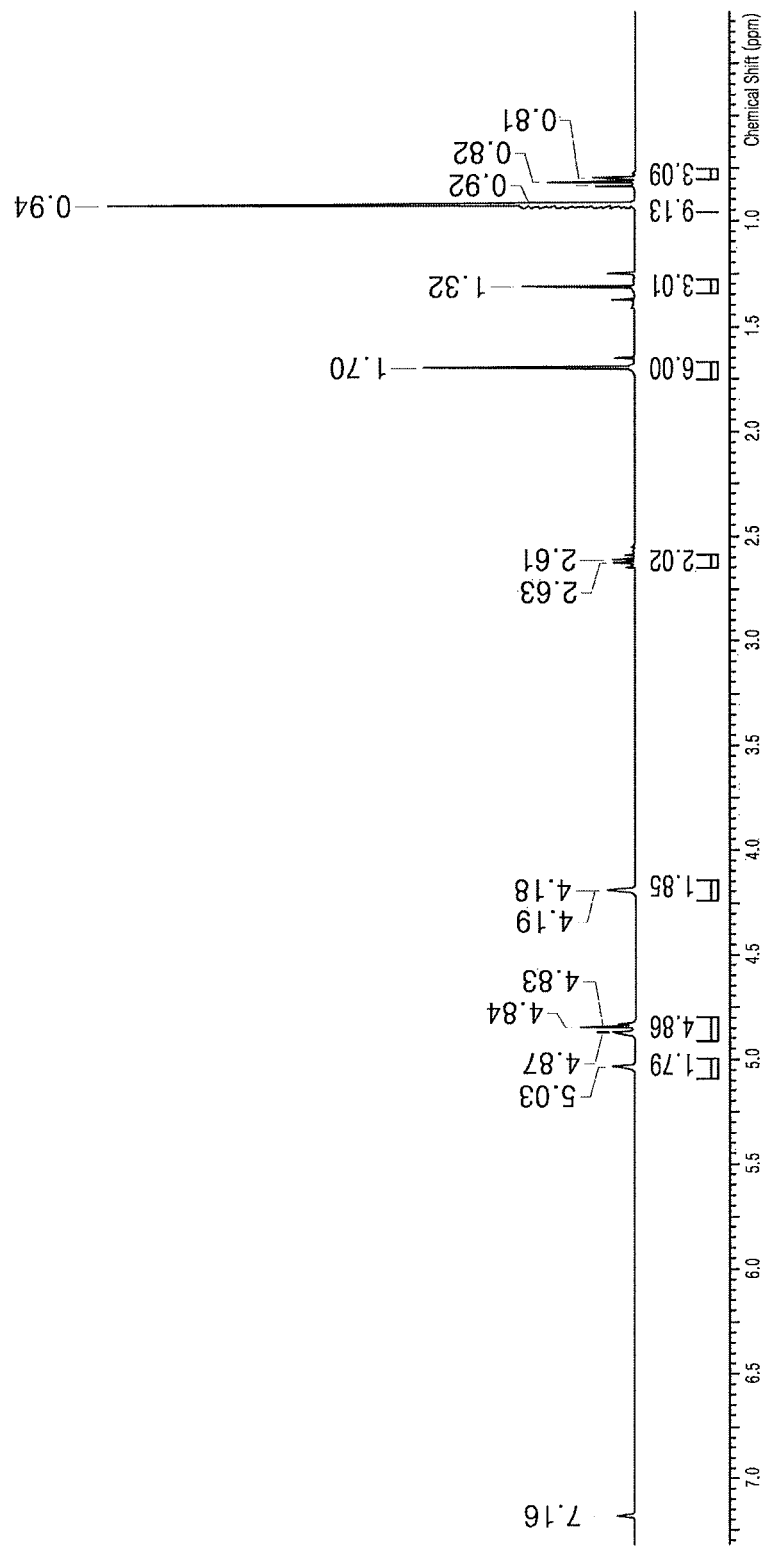
FIG. 14 illustrates a $^1$H-NMR spectrum of bis-methylcyclopentadienyl t-butyl, ethylamidinato niobium (Nb $(MeCp)_2$ ($N^{tBu, Et}$ Me-amd))

FIG. 14 is a $^1$H-NMR spectrum of the material obtained in Example 6. $^1$H-NMR (δ, ppm, C6D6): 4.18-5.03 (m, 8H), 2.61 (q, 2H), 1.70 (s, 6H), 1.32 (s, 3H), 0.94 (s, 9H), 0.82 (t, 3H).

Figure 15:
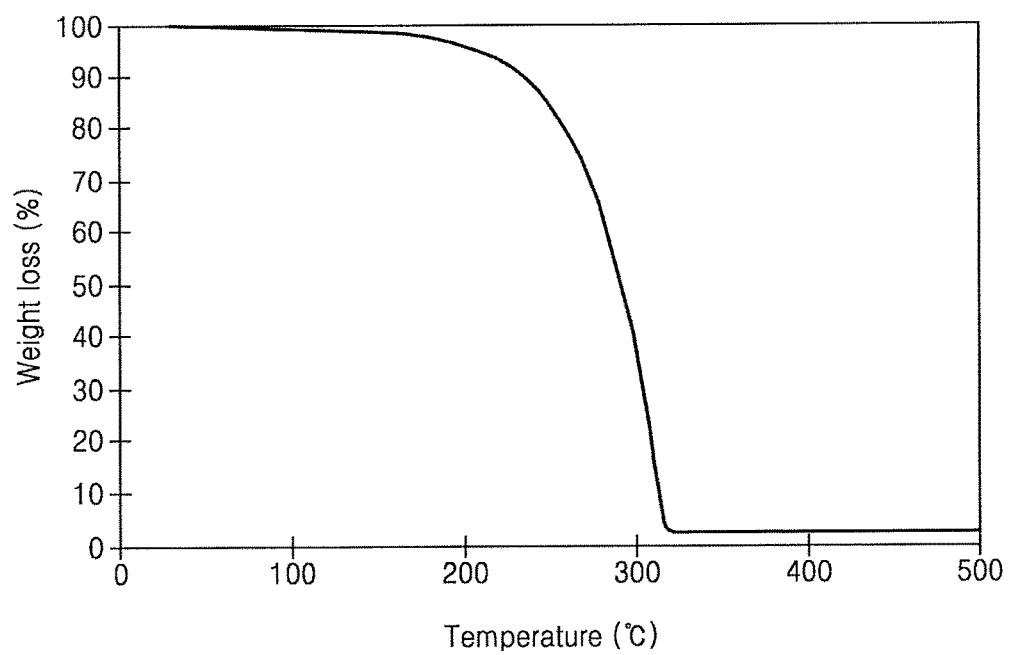
FIG. 15 illustrates a TGA graph depicting the percentage of weight loss with increasing temperature of (Nb$(MeCp)_2$ ($N^{tBu, Et}$ Me-amd))

The solid material obtained in Example 6 was subjected to Open-Cup thermogravimetric analysis at a heating rate of 10° C./min in an atmosphere of nitrogen flowing at 200 mL/min. As a result, the remaining mass of the material was 2.2% (26% in the case of Close-Cup). These results are shown in FIG. 15. A TGA graph of FIG. 15 shows the percentage of weight loss with increasing temperature of the material.

Example 7—Synthesis of bis-ethylcyclopentadienyl diisopropylacetamidinato niobium (Nb(EtCp)$_2$ (N$^{iPr}$ Me-amd))

Methyl lithium (178 mL, 0.28 mol) was slowly added dropwise to a solution in which diisopropyl carbodiimide (36.0 g, 0.28 mol) was dissolved in about 200 mL of THF at −78° C. The components were stirred at room temperature for 5 hours, followed by adding the mixture to a solution in which Nb(EtCp)$_2$(Cl)$_2$ (50 g, 0.14 mol) was dissolved in about 20 mL of THF at −78° C. The mixture was stirred overnight at room temperature. Next, the solvent was removed in a vacuum, and the product was extracted with toluene, thereby obtaining a black liquid. The obtained material was purified by distillation at 220° C. at 20 mTorr (distillation apparatus temperature: 150° C.), thereby obtaining 21.35 g (36%) of a pure black liquid.

Figure 16:
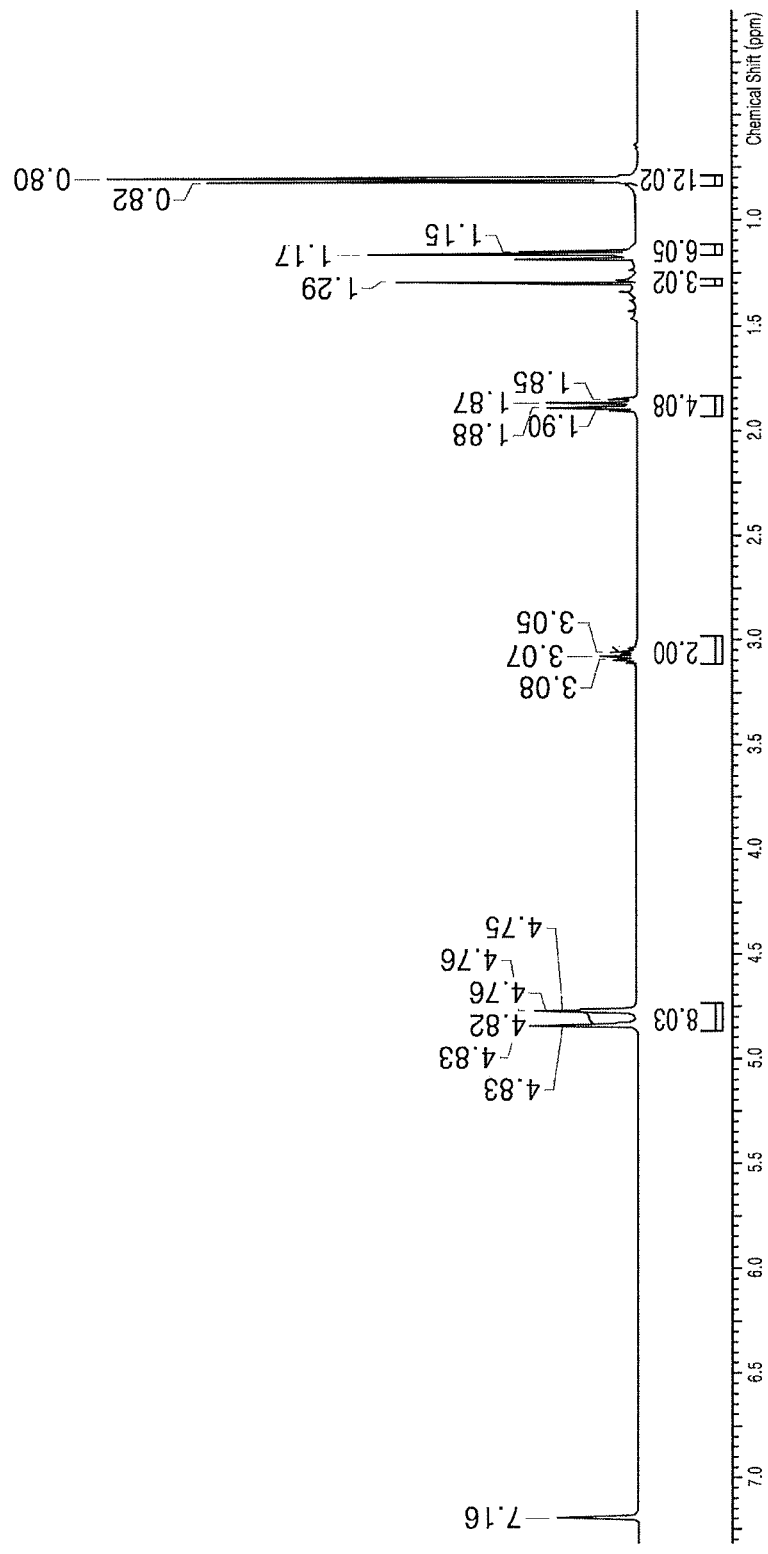
FIG. 16 illustrates a $^1$H-NMR spectrum of bis-ethylcyclopentadienyl diisopropylacetamidinato niobium (Nb $(EtCp)_2(N^{iPr}$ Me-amd))

FIG. 16 is a $^1$H-NMR spectrum of the material obtained in Example 7. $^1$H-NMR (δ, ppm, C6D6): 4.75-4.81 (m, 8H), 3.07 (m, 2H), 1.86 (q, 4H), 1.30 (s, 3H), 1.16 (t, 6H), 0.80 (d, 12H).

Figure 17:
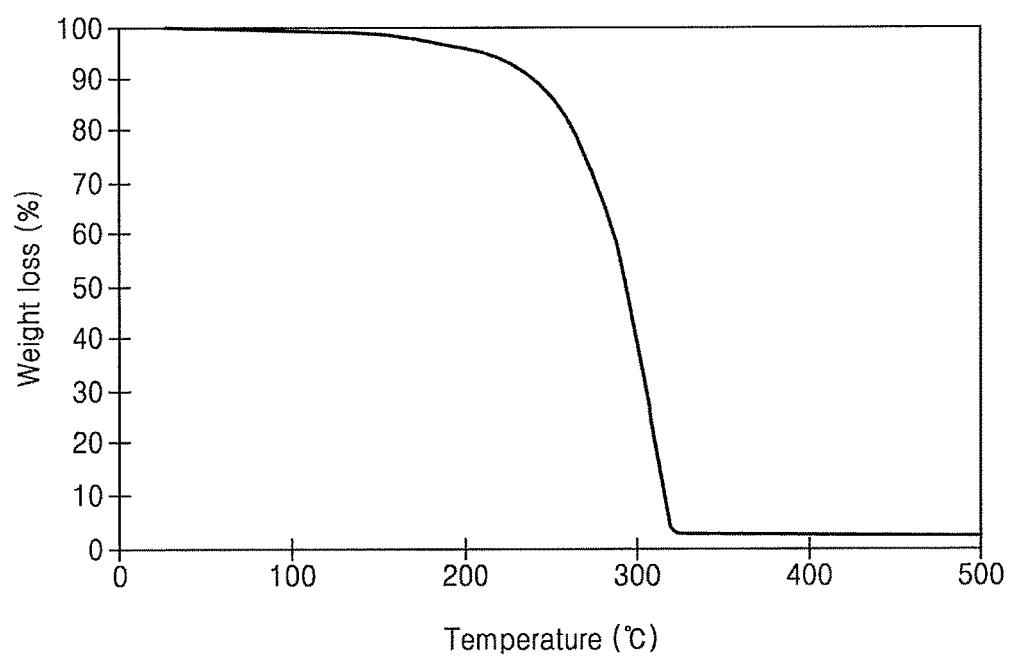
FIG. 17 illustrates a TGA graph depicting the percentage of weight loss with increasing temperature of $Nb(EtCp)_2$ ($N^{iPr}$ Me-amd)

The material obtained in Example 7 was subjected to Open-Cup thermogravimetric analysis at a heating rate of 10° C./min in an atmosphere of nitrogen flowing at 200 mL/min. As a result, the remaining mass of the material was 2.4% (26% in the case of Close-Cup). These results are shown in FIG. 17. A TGA graph of FIG. 17 shows the percentage of weight loss with increasing temperature of the material.

Example 8—Formation of NbN Thin Film (2)

A NbN thin film was formed using Nb(EtCp)$_2$(N$^{iPr}$ Me-amd) synthesized in Example 7. For this purpose, ALD deposition characteristics were evaluated using a Nb(EtCp)$_2$ (N$^{iPr}$ Me-amd) precursor contained in a container heated up to 150° C. and using ammonia corresponding to a co-reactant. A typical ALD process was performed under the condition of a reactor pressure fixed at about 2 Torr using ammonia as a co-reactant.

Figure 18:
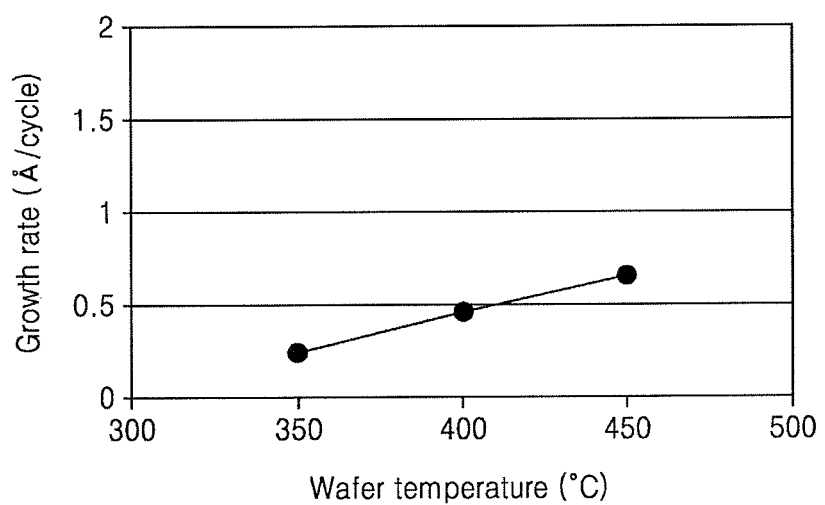
FIG. 18 illustrates a graph depicting a deposition rate of a NbN thin film using $Nb(EtCp)_2(N^{iPr}$ Me-amd)
Figure 19:
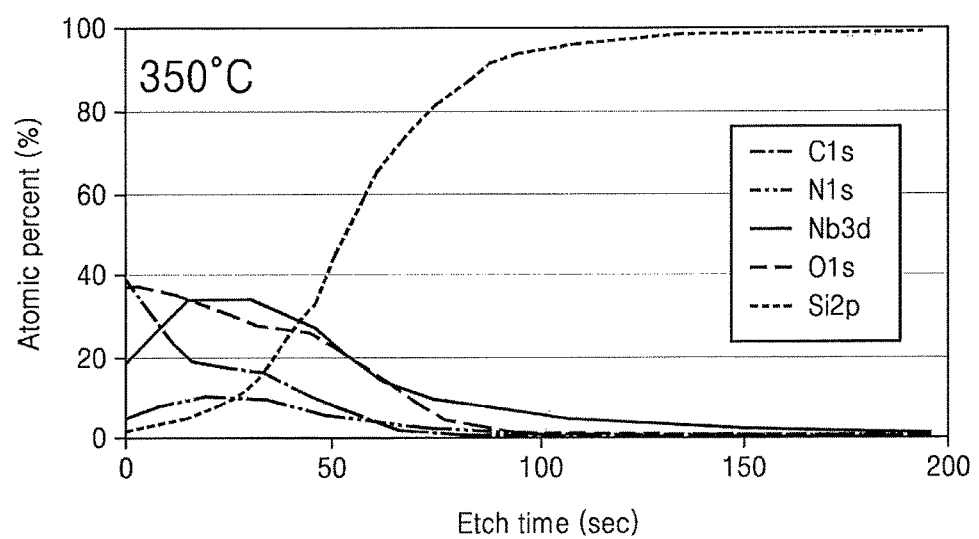
FIG. 19 illustrates a graph showing a result of XPS analysis of a NbN thin film formed at 350° C. using $Nb(EtCp)_2(N^{iPr}$ Me-amd)
Figure 20:
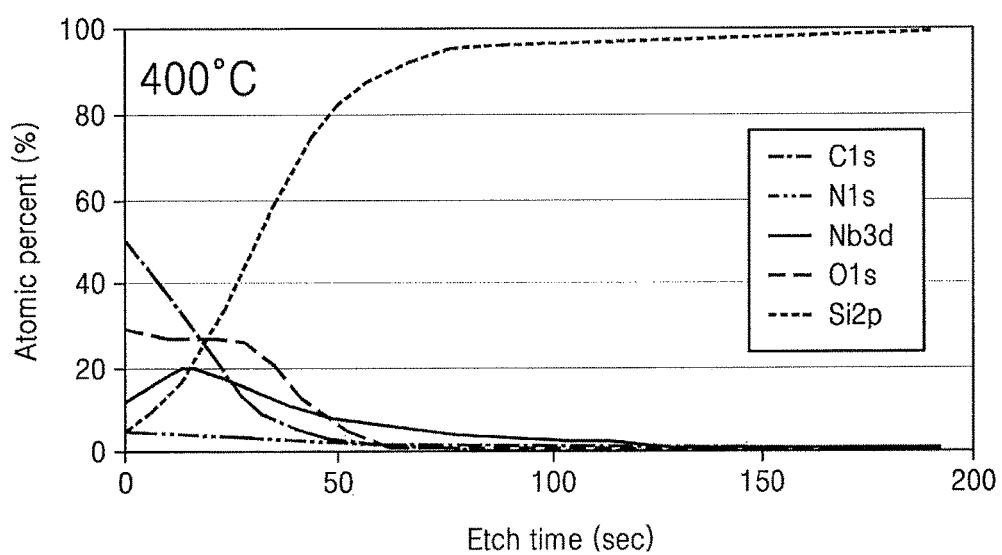
FIG. 20 illustrates a graph depicting a result of XPS analysis of a NbN thin film formed at 400° C. using $Nb(EtCp)_2(N^{iPr}$ Me-amd)

FIG. 18 is a graph depicting a deposition rate of a NbN thin film at a temperature of 300° C. to 450° C. using Nb(EtCp)$_2$(N$^{iPr}$ Me-amd). FIGS. 19 and 20 are graphs respectively showing results of XPS analysis of thin films deposited at 350° C. and 400° C. according to Example 8. Resistivity of the NbN thin film deposited at 350° C. was measured as about 700 μΩ·cm.

Example 9—Synthesis of bis-isopropylcyclopentadienyl diisopropylacetamidinato niobium (Nb(iPrCp)$_2$(N$^{iPr}$ Me-amd))

Methyl lithium (7.4 mL, 11.9 mmol) was slowly added dropwise to a solution in which diisopropyl carbodiimide (1.5 g, 11.9 mmol) was dissolved in about 20 mL of THF at −78° C. The components were stirred at room temperature for 3 hours, followed by adding the mixture to a solution in which Nb(iPrCp)$_2$(Cl)$_2$ (2.64 g, 5.9 mmol) was dissolved in about 20 mL of THF at −78° C. The mixture was stirred overnight at room temperature. Next, the solvent was removed in a vacuum, and the product was extracted with toluene, thereby obtaining a black liquid. The obtained material was purified by vacuum distillation at 190° C. at 75 mTorr (distillation apparatus temperature: 86° C.), thereby obtaining 0.85 g (32%) of a pure black liquid.

Figure 21:
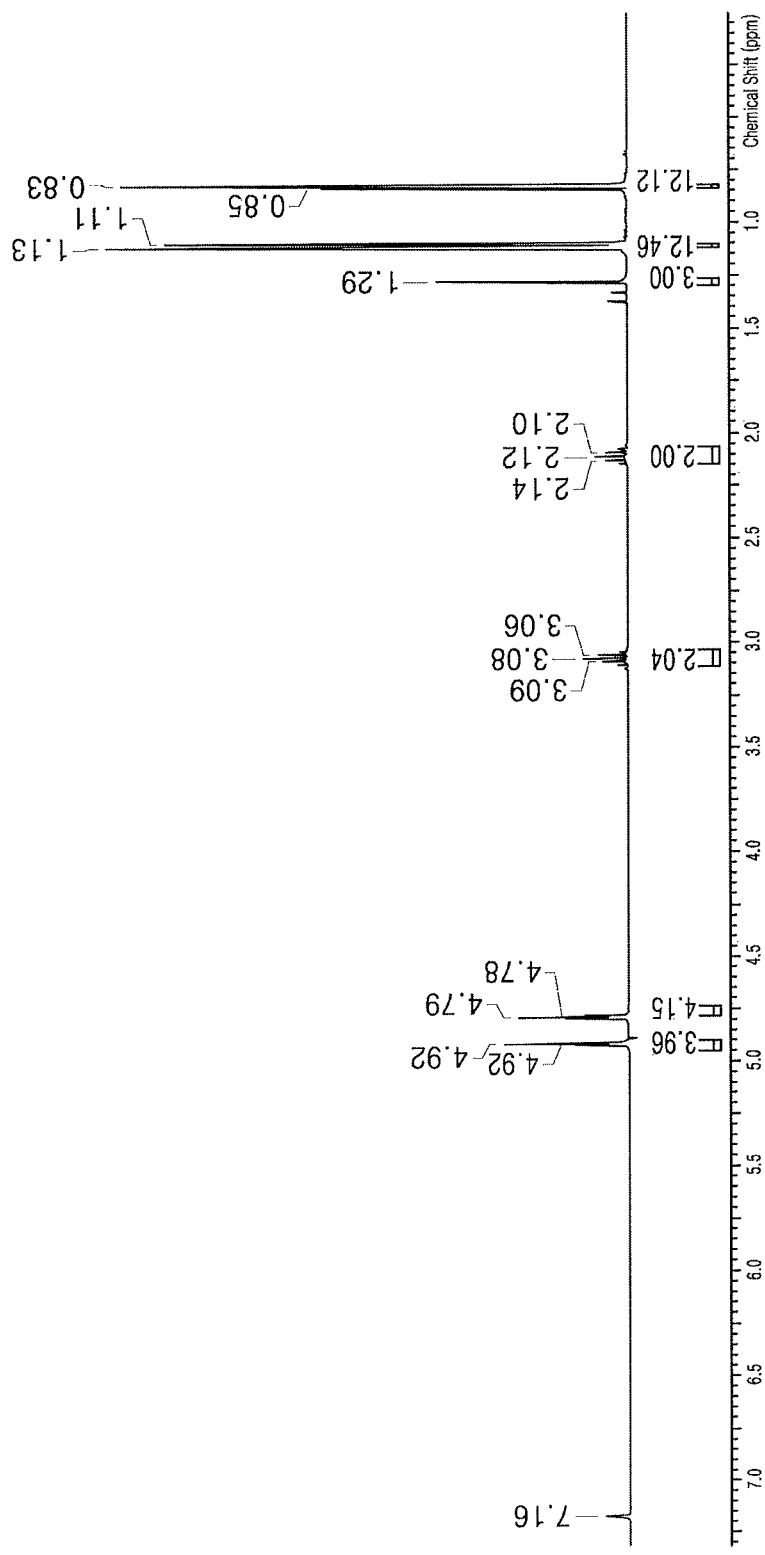
FIG. 21 illustrates a $^1$H-NMR spectrum of bis-isopropylcyclopentadienyl diisopropylacetamidinato niobium (Nb(iPrCp)$_2$(N$^{iPr}$ Me-amd))

FIG. 21 is a $^1$H-NMR spectrum of the material obtained in Example 9. $^1$H-NMR (δ, ppm, C6D6): 4.79-4.92 (m, 8H), 3.08 (m, 2H), 2.12 (m, 2H), 1.29 (s, 3H), 1.11 (d, 12H), 0.83 (d, 12H).

Figure 22:
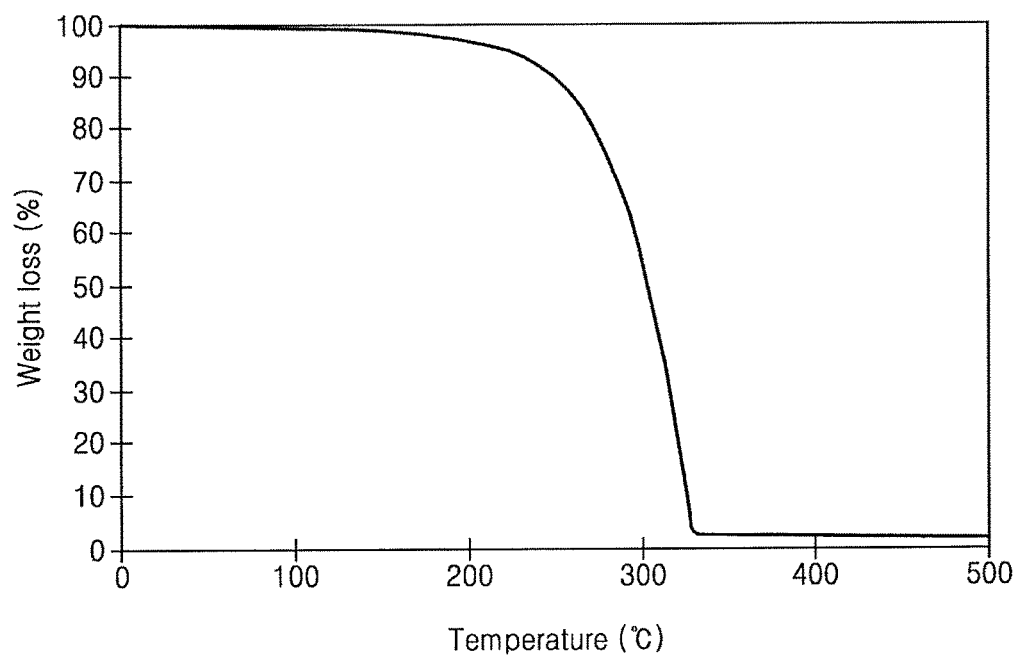
FIG. 22 illustrates a TGA graph depicting the percentage of weight loss with increasing temperature of Nb(iPrCp)$_2$(N$^{iPr}$ Me-amd)

The material obtained in Example 9 was subjected to Open-Cup thermogravimetric analysis at a heating rate of 10° C./min in an atmosphere of nitrogen flowing at 200 mL/min. As a result, the remaining mass of the material was 2.2% (27% in the case of Close-Cup). These results are shown in FIG. 22. A TGA graph of FIG. 22 shows the percentage of weight loss with increasing temperature of the material.

Figure 23A:
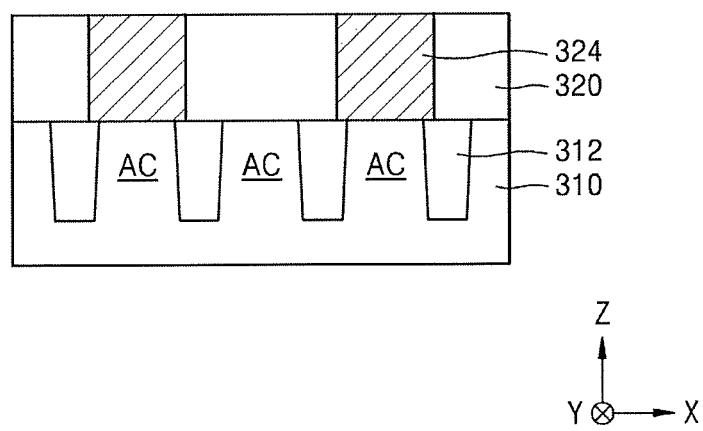
FIGS. 23A to 23J illustrate sectional views of an integrated circuit device shown according to a process order in order to explain a method of fabricating the integrated circuit device according to embodiments.

FIGS. 23A to 23J are sectional views of an integrated circuit device 300 (see FIG. 23J) shown according to a process order in order to explain a method of fabricating the integrated circuit device 300 according to embodiments. Referring to FIG. 23A, an interlayer dielectric 320 is formed on a substrate 310 including a plurality of active regions AC, followed by forming a plurality of conductive regions 324, which penetrate the interlayer dielectric 320 and are respectively connected to the plurality of active regions AC.

The substrate 310 may include a semiconductor such as Si or Ge, or a compound semiconductor such as SiGe, SiC, GaAs, InAs, or InP. In some embodiments, the substrate 310 may include at least one of a Group III-V material and a Group IV material. The Group III-V material may be a binary, ternary, or quaternary compound including at least one Group III atom and at least one Group V atom. The Group III-V material may be a compound including at least one atom of In, Ga, and Al as a Group III atom and at least one atom of As, P, and Sb as a Group V atom. For example, the Group III-V material may be selected from among InP, In$_z$Ga$_{1-z}$As (0≤z≤1), and Al$_z$Ga$_{1-z}$As (0≤z≤1). The binary compound may be, for example, one of InP, GaAs, InAs, InSb, and GaSb. The ternary compound may be one of InGaP, InGaAs, AlInAs, InGaSb, GaAsSb, and GaAsP. The Group IV material may be Si or Ge. However, the Group III-V material and the Group IV material, which can be used for the integrated circuit device according to an example embodiment, are not limited to the examples set forth above. In another embodiment, the substrate 310 may have a silicon on insulator (SOI) structure. The substrate 310 may include a conductive region, for example, an impurity-doped well, or an impurity-doped structure.

The plurality of active regions AC may be defined by a plurality of device isolation regions 312 formed on the substrate 310. The device isolation regions 312 may include a silicon oxide film, a silicon nitride film, a silicon oxynitride film, or combinations thereof.

The interlayer dielectric 320 may include a silicon oxide film.

The plurality of conductive regions 324 may be connected to one terminal of a switching device (not shown) such as a field effect transistor formed on the substrate 310. The plurality of conductive regions 324 may include polysilicon, a metal, a conductive metal nitride, a metal silicide, combinations thereof, etc.

Figure 23B:
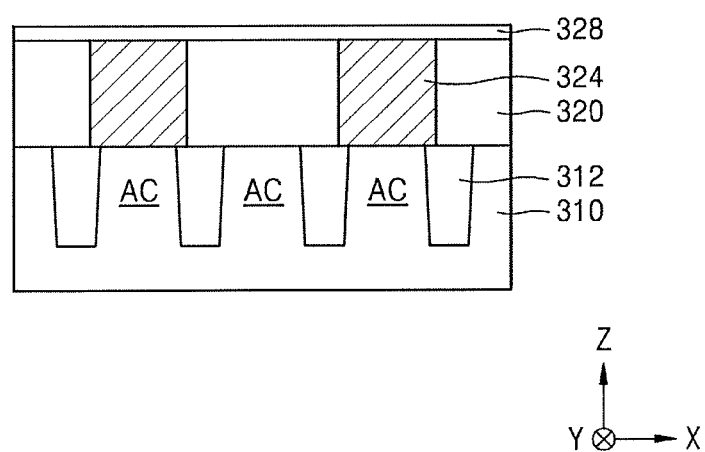

Referring to FIG. 23B, an insulating layer 328 covering the interlayer dielectric 320 and the plurality of conductive regions 324 is formed. The insulating layer 328 may be used as an etch stop layer. The insulating layer 328 may include an insulating material having an etch selectivity with respect to the interlayer dielectric 320 and a mold film 330 (see FIG. 23C) which is formed in a subsequent process. In some embodiments, the insulating layer 328 may include silicon nitride, silicon oxynitride, or combinations thereof. In some embodiments, the insulating layer 328 may have a thickness of about 100 Å to about 600 Å, for example.

Figure 23C:
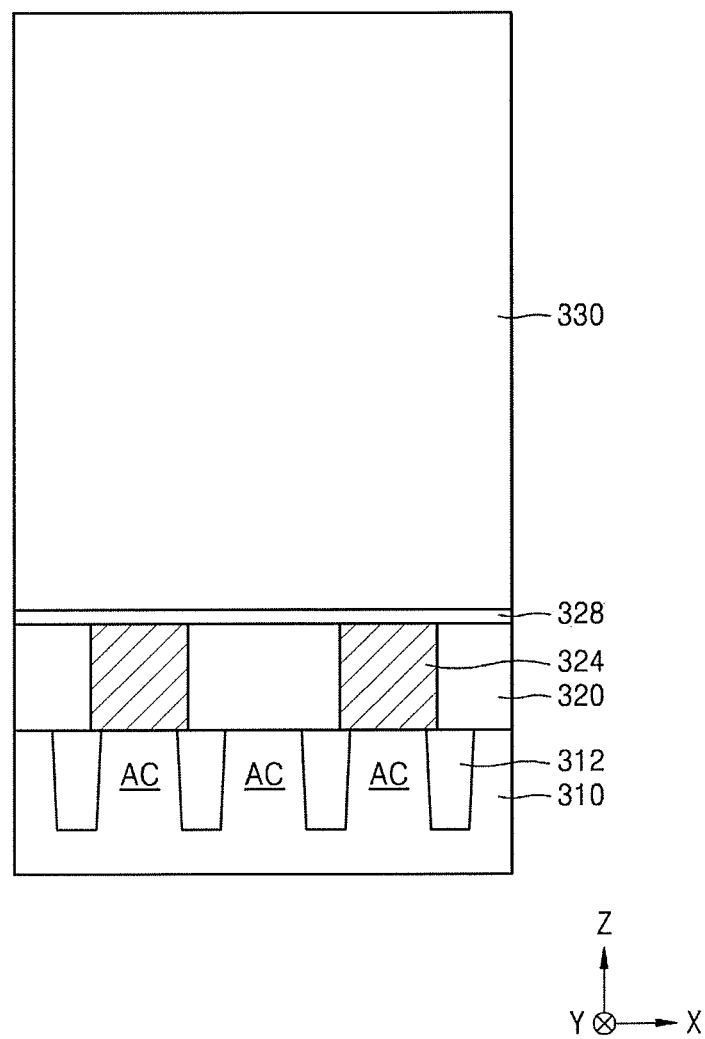

Referring to FIG. 23C, the mold film 330 is formed on the insulating layer 328. In some embodiments, the mold film 330 may include an oxide film. For example, the mold film 330 may include an oxide film such as borophosphosilicate glass (BPSG), phosphosilicate glass (PSG), undoped silicate glass (USG), spin on dielectric (SOD), an oxide film formed by a high density plasma chemical vapor deposition (HDP CVD) process, or the like. To form the mold film 330, a thermal CVD process or a plasma CVD process may be used. In some embodiments, the mold film 330 may have a thickness of about 1,000 Å to about 20,000 Å, for example.

In some embodiments, the mold film 330 may include a support film (not shown). The support film may be formed of a material having an etch selectivity with respect to the mold film 330, and may have a thickness of about 50 Å to about 3,000 Å. The support film may include a material having a relatively low etch rate with respect to an etch atmosphere, for example, with respect to LAL (LAL includes ammonium fluoride (NH$_4$F), hydrofluoric acid (HF), and water) when the mold film 330 is removed by a LAL lift-off process in a subsequent process. In some embodiments, the support film may include silicon nitride, silicon carbonitride, tantalum oxide, titanium oxide, or combinations thereof, for example.

Figure 23D:
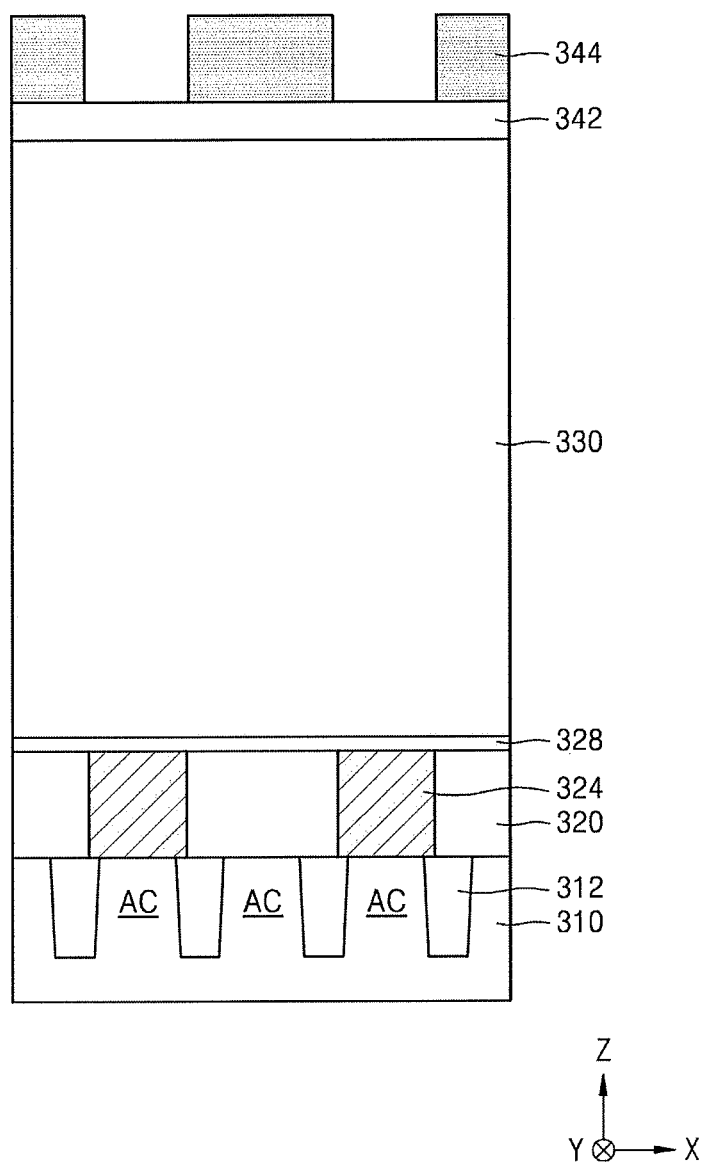

Referring to FIG. 23D, a sacrificial film 342 and a mask pattern 344 are sequentially formed on the mold film 330. The sacrificial film 342 may include an oxide film such as BPSG, PSG, USG, SOD, an oxide film formed by a HDP CVD process, or the like. The sacrificial film 342 may have a thickness of about 500 Å to about 2000 Å. The sacrificial film 342 may serve to protect the support film included in the mold film 330.

The mask pattern 344 may include an oxide film, a nitride film, a polysilicon film, a photoresist film, or combinations thereof. A region in which a lower electrode of a capacitor is formed may be defined by the mask pattern 344.

Figure 23E:
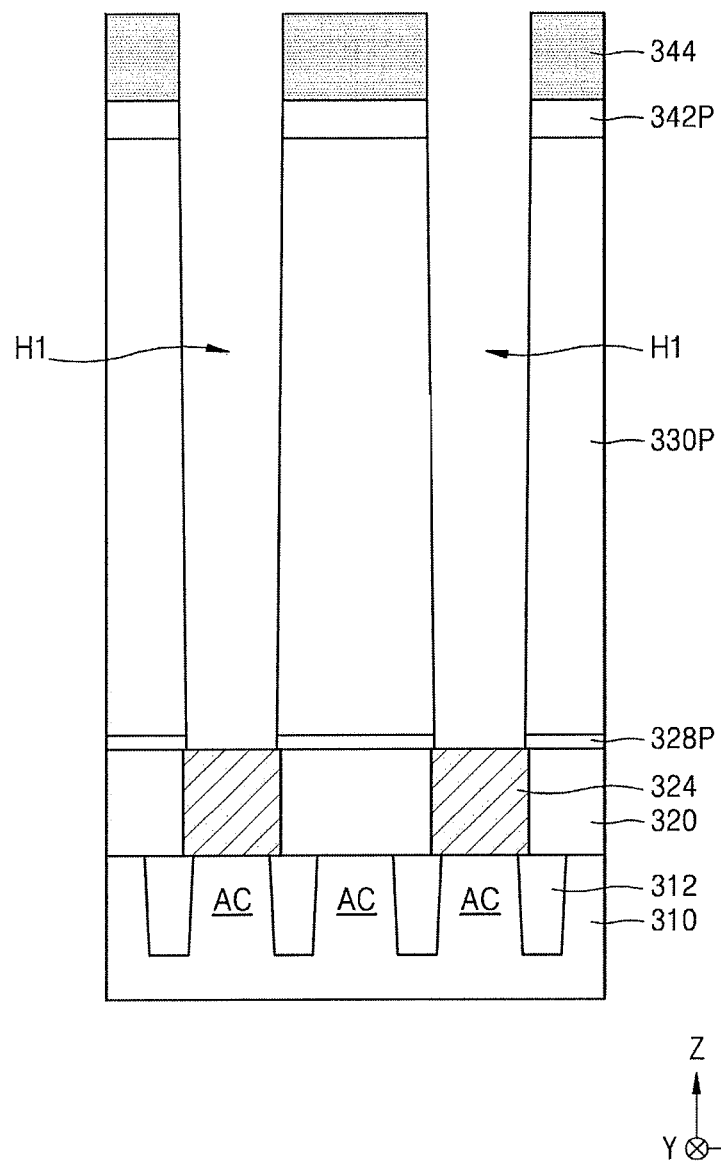

Referring to FIG. 23E, the sacrificial film 342 and the mold film 330 are dry-etched using the mask pattern 344 as an etch mask and using the insulating layer 328 as an etch stop layer, thereby forming a sacrificial pattern 342P and a mold pattern 330P, which define a plurality of holes H1. Here, the insulating layer 328 may also be etched due to overetch, whereby an insulating pattern 328P exposing the plurality of conductive regions 324 may be formed.

Figure 23F:
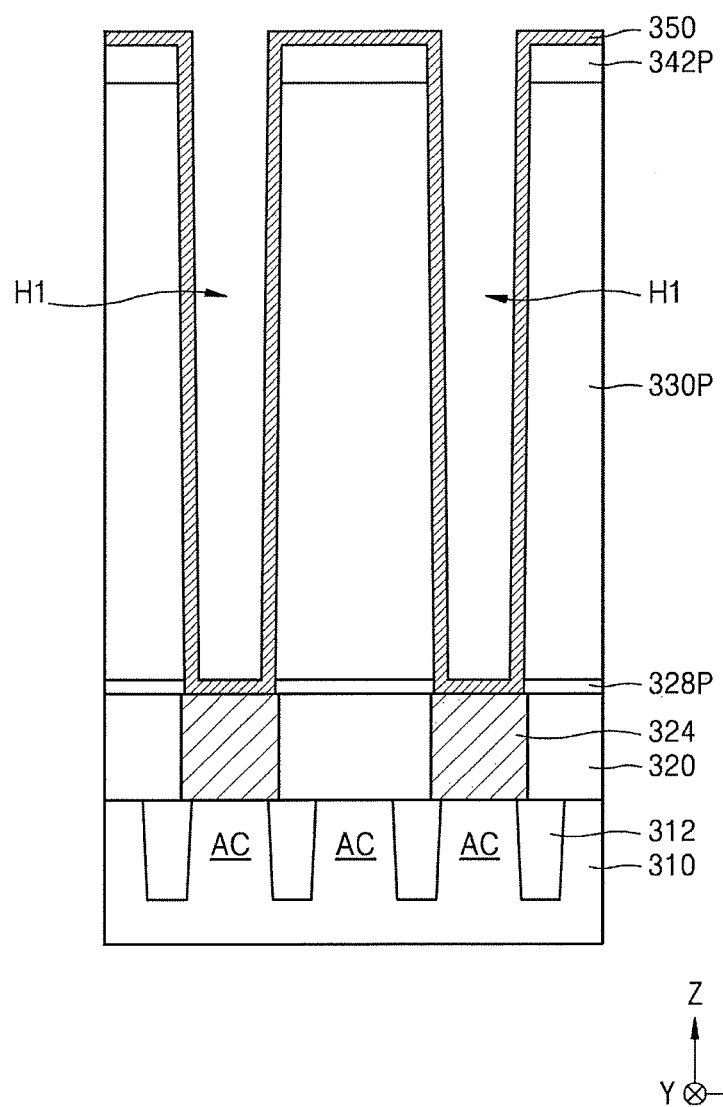

Referring to FIG. 23F, the mask pattern 344 is removed from the resultant of FIG. 23E, followed by forming a conductive film 350 for forming lower electrodes, which covers an inner sidewall of each of the plurality of holes H1, an exposed surface of the insulating pattern 328P, an exposed surface of each of the plurality of conductive regions 324 inside the plurality of holes H1, and an exposed surface of the sacrificial pattern 342P.

The conductive film 350 for forming lower electrodes may be conformally formed on the sidewalls of the plurality of holes H1 such that an inner space of each of the plurality of holes H1 partially remains.

In some embodiments, the conductive film 350 for forming lower electrodes may include a NbN film. In some other embodiments, the conductive film 350 for forming lower electrodes may include combinations of a NbN film and another conductive film. The other conductive film may include a doped semiconductor, a conductive metal nitride, a metal, a metal silicide, a conductive oxide, or combinations thereof. For example, the conductive film 350 for forming lower electrodes may include a NbN film alone, or may include combinations of a NbN film with a conductive film including TiN, TiAlN, TaN, TaAlN, W, WN, Ru, $RuO_2$, $SrRuO_3$, Ir, $IrO_2$, Pt, PtO, SRO ($SrRuO_3$), BSRO ((Ba,Sr)$RuO_3$), CRO ($CaRuO_3$), LSCO ((La,Sr)$CoO_3$), or combinations thereof.

To form a NbN film for forming the conductive film 350 for forming lower electrodes, according to the method of forming the thin film in accordance with embodiments described above, a CVD or ALD process may be performed using the niobium precursor composition that includes the niobium compound represented by Formula (1), and using a reactant containing a N atom.

The niobium compound may be a niobium compound having a structure represented by Chemical Formula 1, 2, or 3. For example, the niobium compound may be $Nb(MeCp)_2$ ($N^{iPr}$ Me-amd), $Nb(EtCp)_2(N^{iPr}$ Me-amd), or $Nb(iPrCp)_2$ ($N^{iPr}$ Me-amd), and the reactant may be $NH_3$.

In some embodiments, the conductive film 350 for forming lower electrodes may not include a NbN film. In these embodiments, the conductive film 350 for forming lower electrodes may include a doped semiconductor, a conductive metal nitride, a metal, a metal silicide, a conductive oxide, or combinations thereof.

Figure 23G:
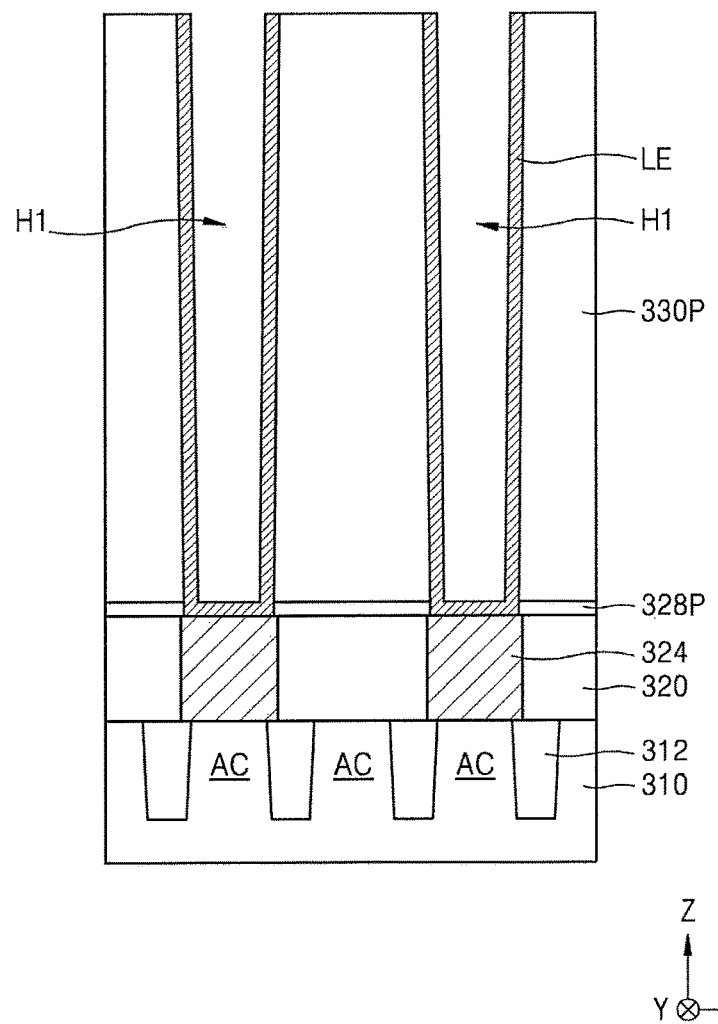

Referring to FIG. 23G, an upper side of the conductive film 350 for forming lower electrodes is partially removed, thereby dividing the conductive film 350 for forming lower electrodes into a plurality of lower electrodes LE. To form the plurality of lower electrodes LE, a portion of the upper side of the conductive film 350 for forming lower electrodes and the sacrificial pattern 342P (see FIG. 23F) may be removed by using an etchback or chemical mechanical polishing (CMP) process until an upper surface of the mold pattern 330P is exposed. The plurality of lower electrodes LE may be connected to the conductive regions 324 through the insulating pattern 328P.

Figure 23H:
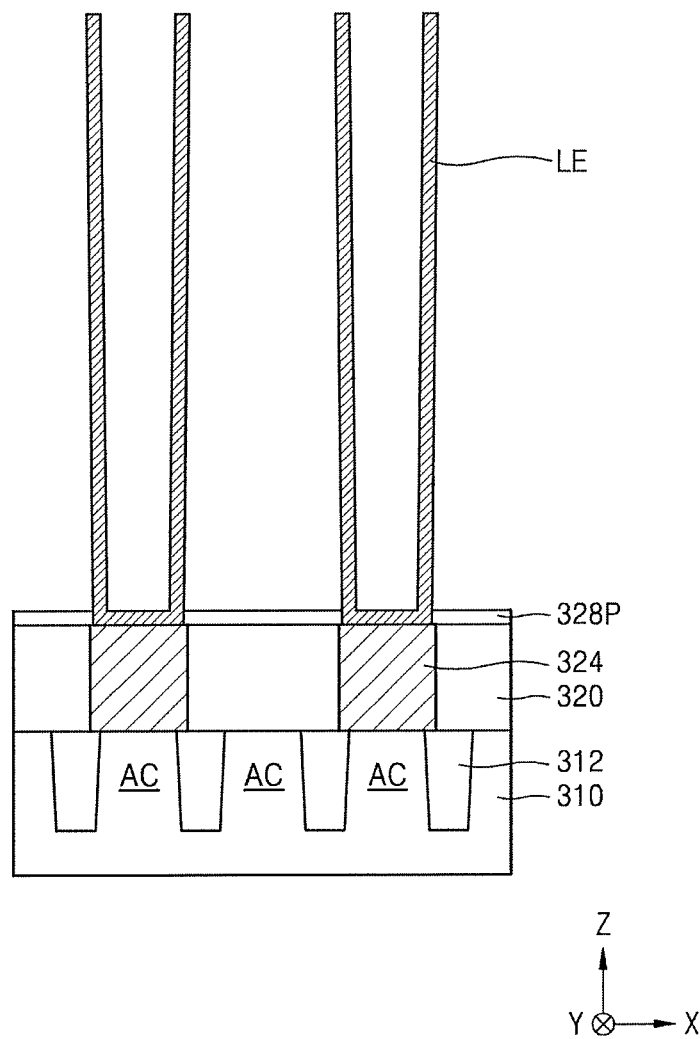

Referring to FIG. 23H, the mold pattern 330P is removed, thereby exposing outer sidewalls of the plurality of lower electrodes LE having cylindrical shapes. The mold pattern 330P may be removed by a lift-off process using LAL or hydrofluoric acid.

Figure 23I:
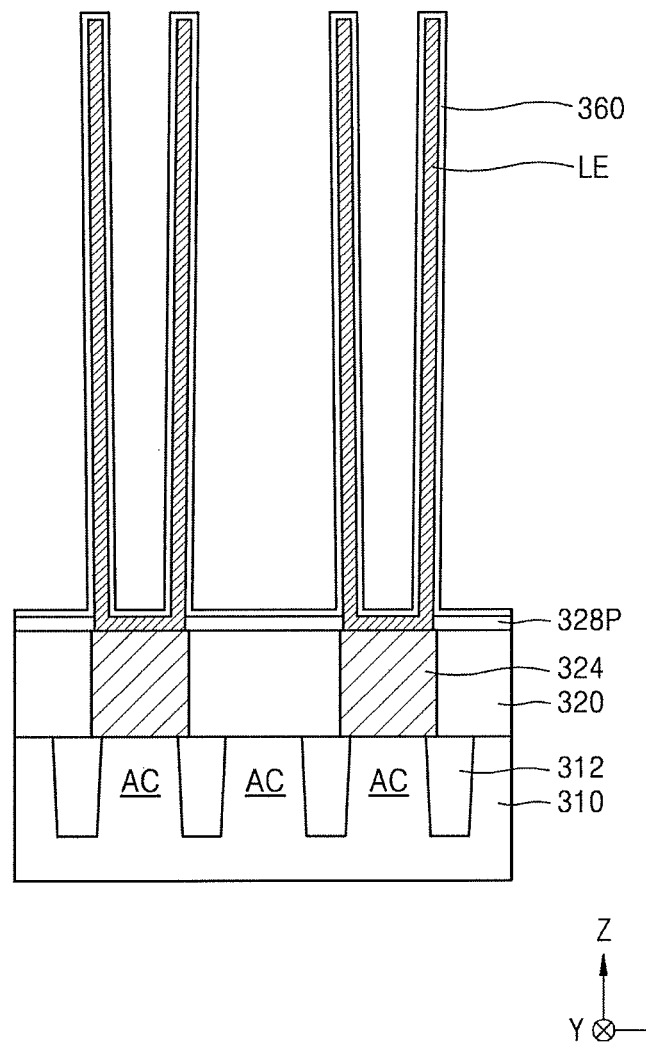

Referring to FIG. 23I, a dielectric film 360 is formed on the plurality of lower electrodes LE. The dielectric film 360 may conformally cover exposed surfaces of the plurality of lower electrodes LE. The dielectric film 360 may be formed by an ALD process.

The dielectric film 360 may include oxide, a metal oxide, nitride, or combinations thereof. In some embodiments, the dielectric film 360 may include a high-K dielectric film having a higher dielectric constant than silicon oxide. For example, the dielectric film 360 may include a $ZrO_2$ film. For example, the dielectric film 360 may include a single layer of a $ZrO_2$ film, or may include multiple layers including a combination of at least one $ZrO_2$ film and at least one $Al_2O_3$ film.

In some embodiments, the dielectric film 360 may have a thickness of about 50 Å to about 150 Å, without being limited thereto.

Figure 23J:
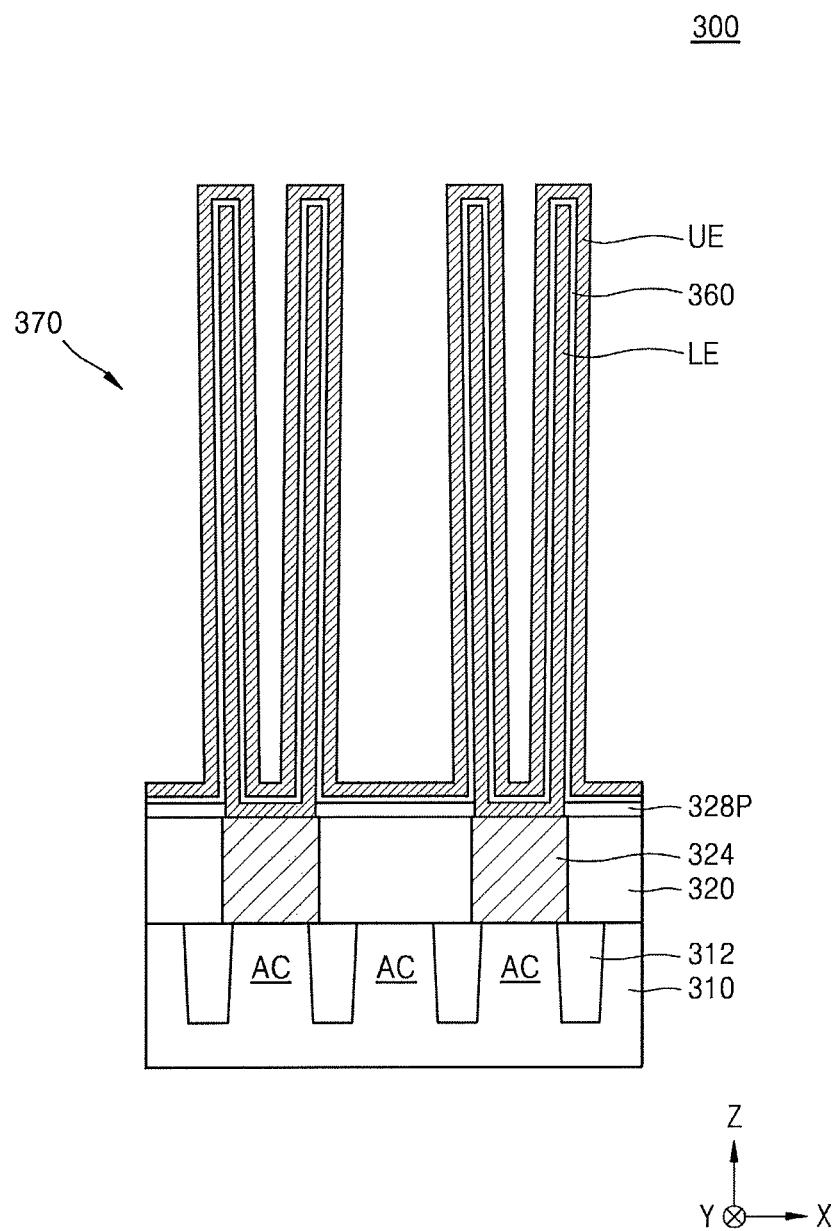

Referring to FIG. 23J, an upper electrode UE is formed on the dielectric film 360. The lower electrode LE, the dielectric film 360, and the upper electrode UE may constitute a capacitor 370. The upper electrode UE may include a NbN film.

To form a NbN film needed for forming the upper electrode UE, according to the method of forming the thin film in accordance with embodiments described above, a CVD or ALD process may be performed using the niobium precursor composition that includes the niobium compound represented by Formula (1), and using a reactant containing a N atom.

The niobium compound may be a niobium compound having a structure represented by Chemical Formula 1, 2, or 3. For example, the niobium compound may be $Nb(MeCp)_2$ ($N^{iPr}$ Me-amd), $Nb(EtCp)_2(N^{iPr}$ Me-amd), or $Nb(iPrCp)_2$ ($N^{iPr}$ Me-amd), and the reactant may be $NH_3$.

In some other embodiments, the upper electrode UE may include combinations of a NbN film and another conductive film. The other conductive film may include a doped semiconductor, a conductive metal nitride, a metal, a metal silicide, a conductive oxide, or combinations thereof. For example, the upper electrode UE may include TiN, TiAlN, TaN, TaAlN, W, WN, Ru, $RuO_2$, $SrRuO_3$, Ir, $IrO_2$, Pt, PtO, SRO ($SrRuO_3$), BSRO ((Ba,Sr)$RuO_3$), CRO ($CaRuO_3$), LSCO ((La,Sr)$CoO_3$), combinations thereof, etc.

Although the method of fabricating the integrated circuit device 300 including the process of forming the cylindrical lower electrode LE has been described with reference to FIGS. 23A to 23J, embodiments are not limited to the examples set forth above. For example, a pillar-type lower electrode having no inner space may be formed instead of the cylindrical lower electrode LE, and the dielectric film 360 and the upper electrode UE may be formed on the pillar-type lower electrode.

According to the method of fabricating the integrated circuit device in accordance with embodiments as described with reference to FIGS. 23A to 23J, in forming the NbN film constituting the upper electrode UE, when the NbN film is formed on the dielectric film 360 including a high-K dielectric film such as a $ZrO_2$ film, the niobium compound according to an example embodiment is used instead of a Cl-containing Nb precursor such as $NbCl_5$ as a Nb precursor, thereby stably forming the NbN film having a relatively high work function without damaging the dielectric film 360. Therefore, a desired device may be realized without the occurrence of leakage current in the capacitor 370 and deteriorating electrical properties of the device.

Figure 24A:
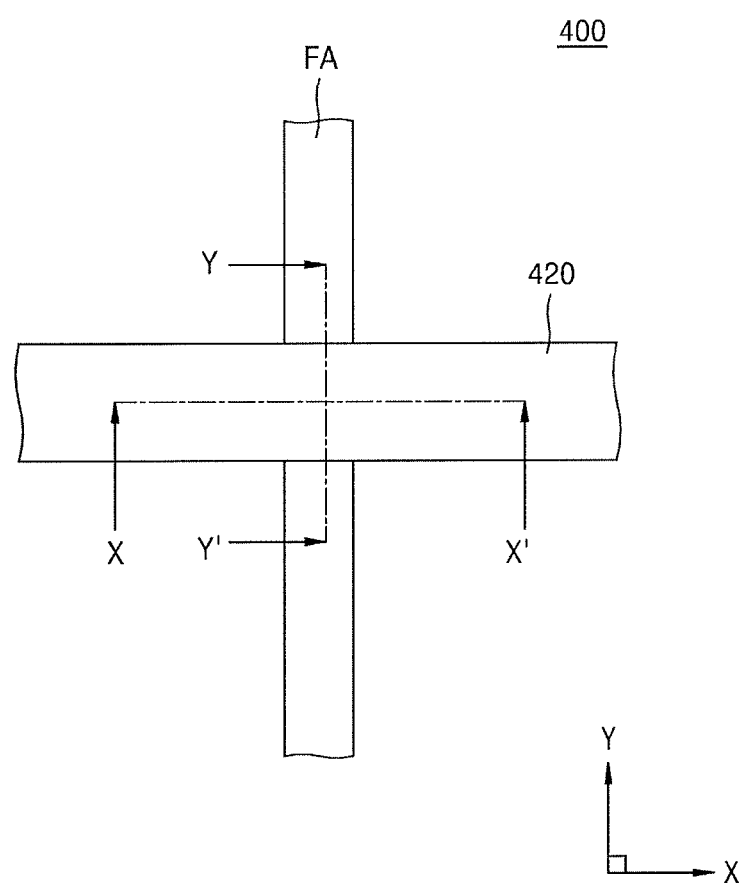
FIGS. 24A to 24C illustrate diagrams for explaining a method of fabricating an integrated circuit device according to other embodiments.
Figure 24B:
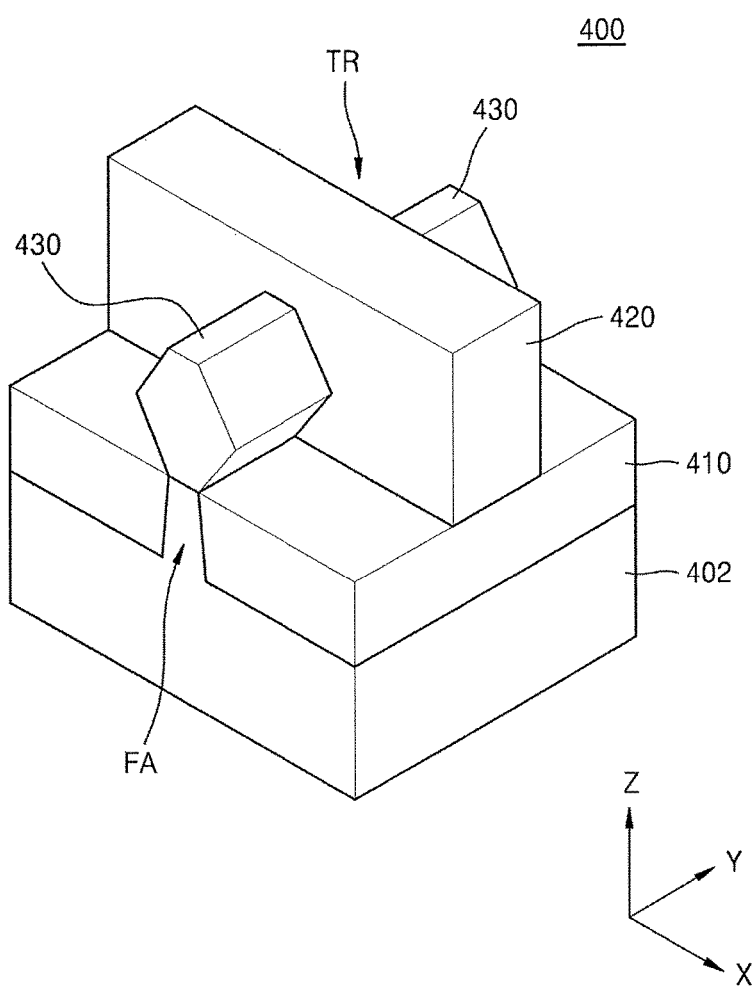
Figure 24C:
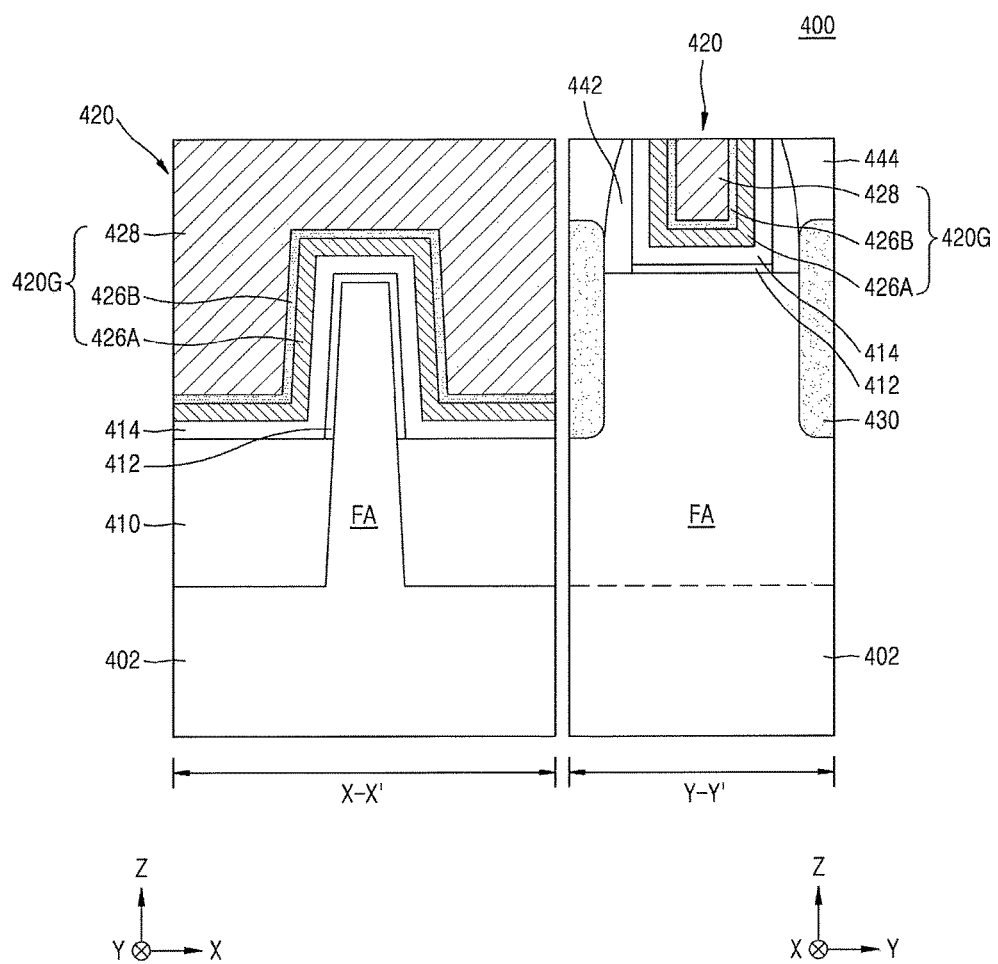

FIGS. 24A to 24C are diagrams for explaining a method of fabricating an integrated circuit device according to other embodiments, FIG. 24A is a plan view of an integrated circuit device 400 that is intended to be formed, FIG. 24B is a perspective view of the integrated circuit device 400 of FIG. 24A, and FIG. 24C respectively shows sectional views of the integrated circuit device 400 taken along lines X-X' and Y-Y' of FIG. 24A.

Referring to FIGS. 24A to 24C, the integrated circuit device 400 includes a fin-type active region FA protruding from a substrate 402. Details of the substrate 402 are mostly the same as described as to the substrate 310 with reference to FIG. 23A.

The substrate 402 may include a Group III-V material or a Group IV material, and thus be used as a channel material allowing a low-power high-speed transistor to be made. If an NMOS transistor is formed on the substrate 402, the substrate 402 may include one of Group III-V materials. For example, the substrate 402 may include GaAs. If a PMOS transistor is formed on the substrate 402, the substrate 402 may include a semiconductor material, for example, Ge providing a higher hole mobility than a Si substrate.

The fin-type active region FA may extend along one direction (Y direction in FIGS. 24A and 24B). A device isolation film 410 covering a lower sidewall of the fin-type active region FA is formed on the substrate 402. The fin-type active region FA protrudes in a fin shape upwards from the device isolation film 410. In some embodiments, the device isolation film 410 may include a silicon oxide film, a silicon nitride film, a silicon oxynitride film, combinations thereof, etc.

On the fin-type active region FA on the substrate 402, a gate structure 420 may extend in a direction (X direction) intersecting with the direction in which the fin-type active region FA extends. A pair of source/drain regions 430 may be formed at both sides of the gate structure 420 on the fin-type active region FA.

The pair of source/drain regions 430 may include a semiconductor layer epitaxially grown on the fin-type active region FA. Each of the pair of source/drain regions 430 may include an embedded SiGe structure including a plurality of epitaxially grown SiGe layers, an epitaxially grown Si layer, or an epitaxially grown SiC layer. In FIG. 24B, although the pair of source/drain regions 430 are shown as having a specific shape, according to an example embodiment, the pair of source/drain regions 430 may have various sectional shapes. For example, the pair of source/drain regions 430 may have various sectional shapes such as circles, ellipses, polygons, and the like.

A MOS transistor TR may be formed in a region in which the fin-type active region FA intersects with the gate structure 420. The MOS transistor TR may include a 3-dimensional structured MOS transistor in which channels are formed on an upper surface and both side surfaces of the fin-type active region FA. The MOS transistor TR may constitute an NMOS transistor or a PMOS transistor.

As shown in FIG. 24C, the gate structure 420 may include an interface layer 412, a high-K dielectric film 414, a first metal-containing layer 426A, a second metal-containing layer 426B, and a gap-fill metal layer 428, which are sequentially formed on a surface of the fin-type active region FA. The first metal-containing layer 426A, the second metal-containing layer 426B, and the gap-fill metal layer 428 of the gate structure 420 may constitute a gate electrode 420G.

An insulating spacer 442 may be formed on both side surfaces of the gate structure 420. An interlayer dielectric 444 covering the insulating spacer 442 may be formed at an opposite side to the gate structure 420 with the insulating spacer 442 interposed between the gate structure 420 and the interlayer dielectric 444.

The interface layer 412 may be formed on a surface of the fin-type active region FA. The interface layer 412 may be formed of an insulating material such as an oxide film, a nitride film, or an oxynitride film. The interface layer 412 may constitute a gate insulating film in conjunction with the high-K dielectric film 414.

The high-K dielectric film 414 may include a material having a greater dielectric constant than a silicon oxide film. For example, the high-K dielectric film 414 may have a dielectric constant of about 10 to about 25. The high-K dielectric film 414 may include a material selected from among zirconium oxide, zirconium silicon oxide, hafnium oxide, hafnium oxynitride, hafnium silicon oxide, tantalum oxide, titanium oxide, barium strontium titanium oxide, barium titanium oxide, strontium titanium oxide, yttrium oxide, aluminum oxide, lead scandium tantalum oxide, lead zinc niobate, and combinations thereof, for example. The high-K dielectric film 414 may be formed by an ALD process.

In some embodiments, the first metal-containing layer 426A may include Nb nitride. For example, the first metal-containing layer 426A may include a NbN film.

To form the NbN film constituting the first metal-containing layer 426A, according to the method of forming the thin film in accordance with embodiments described above, a CVD or ALD process may be performed using the niobium precursor composition that includes the niobium compound represented by Formula (1), and using a reactant containing a N atom.

The niobium compound may be a niobium compound having a structure represented by Chemical Formula 1, 2, or 3. For example, the niobium compound may be $Nb(MeCp)_2(N^{iPr}$ Me-amd), $Nb(EtCp)_2(N^{iPr}$ Me-amd), or $Nb(iPrCp)_2(N^{iPr}$ Me-amd), and the reactant may be $NH_3$.

In some other embodiments, the first metal-containing layer 426A may further include an additional metal-containing layer including Ti nitride, Ta nitride, Ti oxynitride, or Ta oxynitride, in addition to the NbN film. For example, the additional metal-containing layer may include TiN, TaN, TiAlN, TaAlN, TiSiN, or combinations thereof. The additional metal-containing layer may be formed by various deposition methods such as ALD, CVD, physical vapor deposition (PVD), and the like.

In some embodiments, the second metal-containing layer 426B may include an N-type metal-containing layer needed for an NMOS transistor including a Ti or Ta-containing Al compound. For example, the second metal-containing layer 426B may include TiAlC, TiAlN, TiAlCN, TiAl, TaAlC, TaAlN, TaAlCN, TaAl, or combinations thereof.

In some other embodiments, the second metal-containing layer 426B may include a P-type metal-containing layer for a PMOS transistor. For example, the second metal-containing layer 426B may include at least one of Mo, Pd, Ru, Pt, TiN, WN, TaN, Ir, TaC, RuN, and MoN.

The second metal-containing layer 426B may include a single layer or multiple layers. The second metal-containing layer 426B may serve to adjust a work function of the gate structure 420 in conjunction with the first metal-containing layer 426A. A threshold voltage of the gate structure 420 may be adjusted by work function adjustment of the first metal-containing layer 426A and the second metal-containing layer 426B.

The gap-fill metal layer 428 may fill a remaining gate space on the second metal-containing layer 426B when the gate structure 420 is formed by a replacement metal gate (RMG) process. If the remaining gate space on the second metal-containing layer 426B is not present after the second metal-containing layer 426B is formed, the gap-fill metal layer 428 may be omitted instead of being formed on the second metal-containing layer 426B.

The gap-fill metal layer 428 may include a material selected from the group consisting of W, metal nitrides such as TiN and TaN, Al, metal carbides, metal silicides, metal aluminum carbides, metal aluminum nitrides, metal silicon nitrides, and the like.

According to the method of fabricating the integrated circuit device 400 in accordance with embodiments as described with reference to FIGS. 24A to 24C, the NbN film constituting the first metal-containing layer 426A is formed on the high-K dielectric film 414 using the niobium compound according to an example embodiment as a niobium precursor. Therefore, unlike in the case of using a Cl-containing Nb precursor such as $NbCl_5$ as a Nb precursor, the NbN film having a relatively high work function may be stably formed without damaging the high-K dielectric film 414. Therefore, a desired device may be realized without the occurrence of leakage current of a transistor or deteriorating electrical properties of the transistor.

Although the method of fabricating the integrated circuit device including a FinFET having a 3-dimensional structured channel has been described with reference to FIGS. 24A to 24C, it will be understood by those skilled in the art that methods of fabricating integrated circuit devices including a planar MOSFET having features according to an example embodiment may be provided through various changes and modifications.

Figure 25:
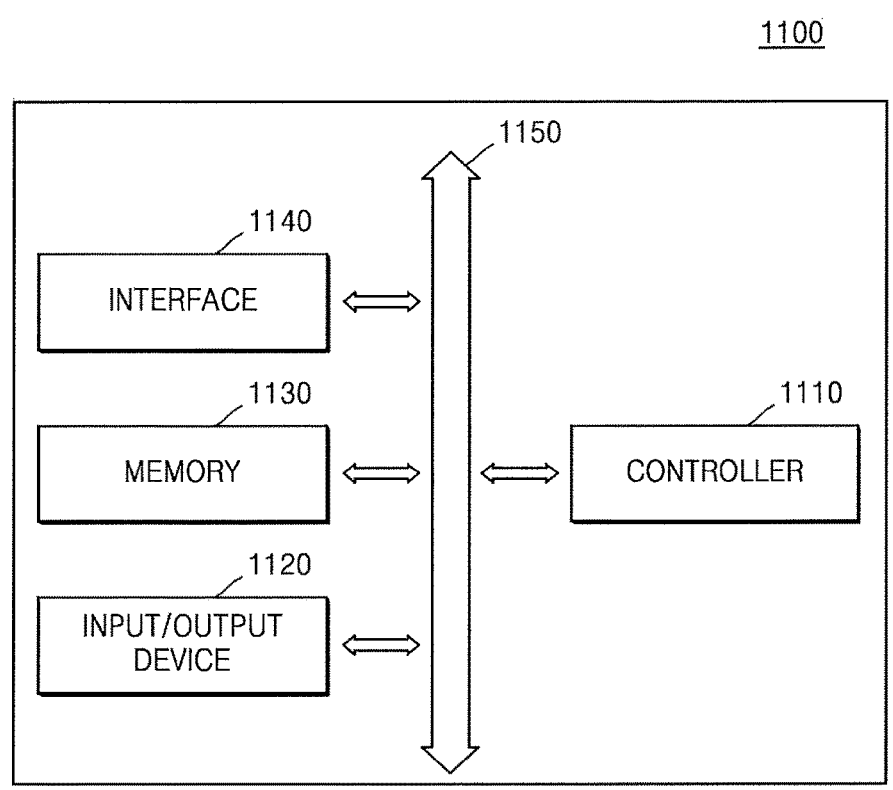
FIG. 25 illustrates a block diagram showing main components of an electronic device according to embodiments.

FIG. 25 is a block diagram showing main components of an electronic device 1100 according to embodiments. The electronic device 1100 includes a controller 1110, an input/output device 1120, a memory 1130, and an interface 1140. The electronic device 1100 may be a mobile system, or a system transmitting or receiving information. In some embodiments, the mobile system may include at least one of a personal digital assistant (PDA), a portable computer, a web tablet, a wireless phone, a mobile phone, a digital music player, and a memory card. In some embodiments, the controller 1110 is a microprocessor, a digital signal processor, or a micro-controller.

The input/output device 1120 is used for data input and output of the electronic device 1100. The electronic device 1100 may be connected to devices external to the electronic device 1100, for example, a personal computer or a network by using the input/output device 1120, and exchange data with the external devices. In some embodiments, the input/output device 1120 is a keypad, a keyboard, a touch screen, or a display.

In some embodiments, the memory 1130 stores code and/or data for operations of the controller 1110. In some other embodiments, the memory 1130 stores data processed by the controller 1110. At least one of the controller 1110 and the memory 1130 includes the niobium-containing film formed by the method of forming the thin film according to an example embodiment, the integrated circuit device 300 described with reference to FIGS. 23A to 23J, or the integrated circuit device 400 described with reference to FIGS. 24A to 24C.

The interface 1140 serves as a data transmitting path between the electronic device 1100 and other devices external to the electronic device 1100. The controller 1110, the input/output device 1120, the memory 1130, and the interface 1140 may communicate with each other through a bus 1150.

The electronic device 1100 may be included in mobile phones, MP3 players, navigation systems, portable multimedia players (PMPs), solid state disks (SSDs), or household appliances.

By way of summation and review, a metal nitride film, for example, a niobium nitride thin film, which provides a relatively high work function, may be used in a semiconductor device. In forming a NbN thin film, a niobium precursor is desired which is advantageous in terms of process stability and mass productivity without damaging an underlayer.

As described above, the niobium compound used in the method of forming the thin film according to an example embodiment has a relatively low melting point, can be delivered in a liquid state, and exhibits excellent reactivity with a nitrogen-containing reactant that is used to form a NbN thin film. In addition, delivery of the niobium compound may be facilitated when the niobium compound is used for a process of forming a NbN thin film. Thus, the niobium compound may be suitable for being used as a niobium precursor for forming a niobium-containing thin film in a thin film deposition process, such as atomic layer deposition (ALD), chemical vapor deposition (CVD), or the like, in which a source compound is supplied in a vaporized state. The niobium-containing film formed by the method of forming the thin film according to an example embodiment may be limited to a relatively low amount of impurities. Thus, the niobium-containing film may have an improved density, and thus may provide an effect of improving leakage current. In particular, the niobium compound according to an example embodiment may not contain an element, for example, the element chlorine (Cl), that may cause damage to an underlayer, for example, a high-K dielectric film, on which the niobium-containing film is formed. Thus, the Nb-containing film having a relatively high work function may be stably formed without damaging an underlayer during the process of forming the thin film using the niobium compound according to an example embodiment. Therefore, an integrated circuit device having desired properties may be realized without the occurrence of leakage current or deterioration of electrical properties.

Embodiments may provide a method of forming a thin film, which may provide desired electrical properties using a niobium compound capable of providing excellent process stability and mass productivity without damaging an underlayer. Embodiments may also provide a method of fabricating an integrated circuit device having desired electrical properties using a niobium compound capable of providing excellent process stability and mass productivity.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A method of forming a thin film, the method comprising:

forming a niobium-containing film on a substrate by using a niobium precursor composition and a reactant, the niobium precursor composition including a niobium compound represented by Formula (1):

$Nb(R_5Cp)_2(L)$  Formula (1)

wherein, in Formula (1), each R is independently H, a C1 to C6 alkyl group, or $R^1{}_3Si$, with each $R^1$ being independently H or a C1 to C6 alkyl group, Cp is a cyclopentadienyl group, and L is a formamidinate, an amidinate, or a guanidinate.

2. The method as claimed in claim 1, wherein the niobium compound has one of Chemical Formulae 1, 2, and 3:

[Chemical Formula 1]

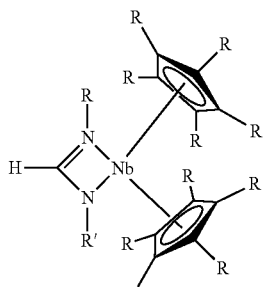

[Chemical Formula 2]

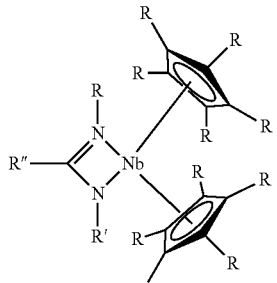

[Chemical Formula 3]

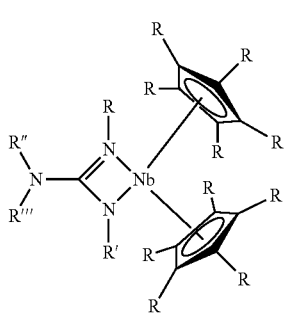

wherein R, R', R", and R'" are each independently H, a C1 to C6 alkyl group, or $R^1{}_3Si$, with each $R^1$ being defined as in Formula (1).

3. The method as claimed in claim 1, wherein the niobium precursor composition consists essentially of the niobium compound represented by Formula (1).

4. The method as claimed in claim 1, wherein the niobium precursor composition includes the niobium compound represented by Formula (1), and impurities including an organic compound, a metal, or combinations thereof.

5. The method as claimed in claim 1, wherein the reactant is selected from among $N_2$, $NH_3$, $N_2H_4$, $N(SiH_3)_3$, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$, $(CH_3)HNNH_2$, $(CH_3)_2NNH_2$, phenylhydrazine, pyrazoline, radicals thereof, and mixtures thereof.

6. The method as claimed in claim 1, wherein the forming of the niobium-containing film includes:

vaporizing the niobium precursor composition which includes the niobium compound represented by Formula (1);

forming a Nb source adsorption layer on the substrate by supplying the vaporized niobium precursor composition onto the substrate; and supplying the reactant onto the Nb source adsorption layer.

7. The method as claimed in claim 6, wherein the forming of the niobium-containing film further includes plasma-treating the vaporized niobium precursor composition, before the supplying of the vaporized niobium precursor composition onto the substrate.

8. The method as claimed in claim 6, wherein the forming of the niobium-containing film further includes plasma-treating the reactant, before the supplying of the reactant onto the Nb source adsorption layer.

9. The method as claimed in claim 1, wherein the forming of the niobium-containing film includes simultaneously supplying the niobium precursor composition and the reactant, the niobium precursor composition including the niobium compound represented by Formula (1).

10. The method as claimed in claim 9, wherein the forming of the niobium-containing film further includes plasma-treating at least one of the niobium precursor composition and the reactant, during the simultaneously supplying of the niobium precursor composition and the reactant.

11. The method as claimed in claim 1, wherein the niobium compound is a liquid at room temperature.

12. A method of fabricating an integrated circuit device, the method comprising:

forming a lower structure on a substrate; and forming a niobium-containing film on the lower structure by using a niobium precursor composition and a reactant, the niobium precursor composition including a niobium compound represented by Formula (1):

$$Nb(R_5Cp)_2(L) \qquad \text{Formula (1)}$$

wherein, in Formula (1), each R is independently H, a C1 to C6 alkyl group, or $R^1{}_3Si$, with each $R^1$ being independently H or a C1 to C6 alkyl group, Cp is a cyclopentadienyl group, and L is a formamidinate, an amidinate, or a guanidinate.

13. The method as claimed in claim 12, wherein the niobium compound has one of Chemical Formulae 1, 2, and 3:

[Chemical Formula 1]

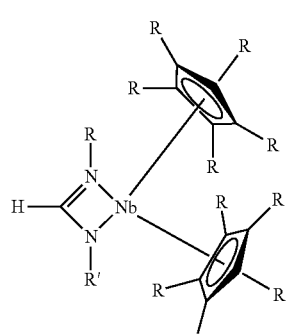

[Chemical Formula 2]

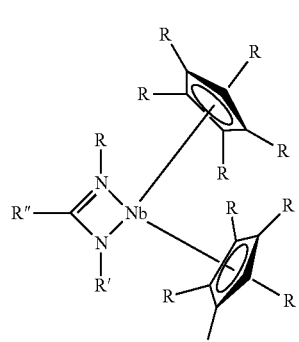

-continued

[Chemical Formula 3]

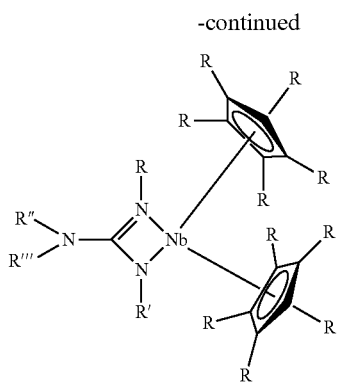

wherein R, R', R", and R'" are each independently H, a C1 to C6 alkyl group, or $R^1_3Si$, with each $R^1$ being defined as in Formula (1).

14. The method as claimed in claim 12, wherein the forming of the lower structure includes forming a dielectric film having a higher dielectric constant than silicon oxide, and
the forming of the niobium-containing film includes forming a NbN film on the dielectric film.

15. The method as claimed in claim 12, wherein the forming of the lower structure includes:
forming a fin active region protruding upwards from the substrate;
forming an interface layer on a surface of the fin active region; and
forming a dielectric film on the interface layer, and
wherein the forming of the niobium-containing film includes forming a NbN film on the dielectric film.

16. A method of forming a semiconductor device, the method comprising:
vaporizing a niobium compound represented by Formula (1) and supplying the vaporized niobium compound to a substrate; and
reacting the niobium compound with a nitrogen-containing reactant to form an electrically conductive niobium nitride layer on the substrate, $$Nb(R_5Cp)_2(L) \qquad \text{Formula (1)}$$

wherein, in Formula (1),
each R is independently H, a C1 to C6 alkyl group, or $R^1_3Si$, with each $R^1$ being independently H or a C1 to C6 alkyl group,
Cp is a cyclopentadienyl group, and
L is a formamidinate, an amidinate, or a guanidinate.

17. The method as claimed in claim 16, wherein the substrate has a dielectric layer, and the niobium nitride layer is formed directly on the dielectric layer.

18. The method as claimed in claim 17, wherein the dielectric layer includes zirconium oxide.

19. The method as claimed in claim 17, wherein the semiconductor device includes a capacitor having a first electrode, a second electrode, and a dielectric between the first and second electrodes, at least one of the first and second electrodes including the niobium nitride layer, and the dielectric including the dielectric layer.

20. The method as claimed in claim 17, wherein the semiconductor device includes a transistor having a gate electrode, the gate electrode including the niobium nitride layer.

* * * * *